United States Patent
Kang-Mieler et al.

(10) Patent No.: US 10,980,882 B2
(45) Date of Patent: Apr. 20, 2021

(54) BIODEGRADABLE MICROSPHERE-HYDROGEL OCULAR DRUG DELIVERY SYSTEM

(71) Applicant: Jennifer J. Kang-Mieler, Winnetka, IL (US)

(72) Inventors: Jennifer J. Kang-Mieler, Winnetka, IL (US); Eric Brey, Chicago, IL (US); Victor Perez-Luna, Naperville, IL (US); Bin Jiang, Chicago, IL (US); Christian Osswald, Wheeling, IL (US)

(73) Assignee: Jennifer J. Kang-Mieler, Winnetka, IL (US)

( * ) Notice: Subject to any disclaimer, the term of this patent is extended or adjusted under 35 U.S.C. 154(b) by 293 days.

(21) Appl. No.: 15/273,098

(22) Filed: Sep. 22, 2016

(65) Prior Publication Data

US 2017/0087248 A1 Mar. 30, 2017

Related U.S. Application Data

(60) Provisional application No. 62/232,545, filed on Sep. 25, 2015.

(51) Int. Cl.

| *A61K 41/00* | (2020.01) |
|---|---|
| *A61K 9/00* | (2006.01) |
| *A61K 47/34* | (2017.01) |
| *A61K 9/06* | (2006.01) |
| *A61K 9/50* | (2006.01) |
| *A61K 38/18* | (2006.01) |
| *A61K 47/36* | (2006.01) |
| *C07K 16/22* | (2006.01) |
| *A61K 39/00* | (2006.01) |

(52) U.S. Cl.
CPC ........ *A61K 41/0028* (2013.01); *A61K 9/0048* (2013.01); *A61K 9/06* (2013.01); *A61K 9/5031* (2013.01); *A61K 9/5036* (2013.01); *A61K 9/5084* (2013.01); *A61K 38/1866* (2013.01); *A61K 47/34* (2013.01); *A61K 47/36* (2013.01); *C07K 16/22* (2013.01); *A61K 2039/505* (2013.01); *C07K 2317/24* (2013.01); *C07K 2317/55* (2013.01)

(58) Field of Classification Search
CPC .... A61K 41/0028; A61K 9/0048; A61K 9/06; A61K 9/5031; A61K 9/5036; A61K 9/5084; A61K 38/1866; A61K 47/34; A61K 47/36; A61K 2039/505; C07K 16/22; C07K 2317/24; C07K 2317/55
See application file for complete search history.

(56) References Cited

U.S. PATENT DOCUMENTS

| 6,287,588 | B1 * | 9/2001 | Shih .................. A61K 9/06 424/426 |
|---|---|---|---|
| 6,962,716 | B1 * | 11/2005 | King .................. A61K 9/1647 424/489 |
| 2003/0223957 | A1 | 12/2003 | Schwartz et al. |
| 2004/0131838 | A1 | 7/2004 | Serra et al. |
| 2009/0232871 | A1 | 9/2009 | Hitz et al. |
| 2010/0111984 | A1 | 5/2010 | D'Souza |
| 2014/0065226 | A1 | 3/2014 | Brey et al. |
| 2014/0242176 | A1 * | 8/2014 | Robledo ............ A61K 31/7048 424/490 |

FOREIGN PATENT DOCUMENTS

WO    WO 03/096876 A2    11/2003
WO    WO 2009/068708    *   6/2009

OTHER PUBLICATIONS

Parente Duena et al. WO 2009/068708, published: Jun. 4, 2009; English machine translation obtained on Feb. 2, 2018.*
Einmahl et al., A Novel Route of Ocular Drug Delivery: Suprachoroidal Injections of a Sustained Release System, Proceed. Int'l. Symp. Control. Rel. Bioact. Mater., 28 (2001), 293-294.*
Drapala, P. W. el, al., "Role of Thermo-responsiveness and Poly (ethylene glycol) Diacrylate Cross-link Density on Protein Release from Poly (N-isopropylacrylamide) Hydrogels," Journal of Biomaterials Science, Jan. 2010, pp. 1-17.
Drapala, P. W. et al., "The Effect of Glutathione as Chain Transfer Agent in PNIPAAm-Based Thermoresponsive Hydrogels for Controlled Release of Proteins," Pharmaceutical Research, Sep. 2013, pp. 740-753.
Kang-Derwent J. et al., "Thermoresponsive Hydrogels as a New Ocular Drug Delivery Platform to the Posterior Segment of the Eye," Trans Am Ophthahnol Soc, Feb. 2008, pp. 206-214.
Kang-Mieler, J. et al., "Advances in ocular drug delivery: emphasis on the posterior segment," Expert Opinion, May 2014, pp. 1646-1660.
Osswald, C. R. et al., "Controlled and Extended Release of a Model Protein from a Microsphere-Hydrogel Drug Delivery System," Annals of Biomedical Engineering, Apr. 2015, pp. 2607-2617.
Osswald, C.R. et al., "Controlled and Extended In Vitro Release of Bioactive Anti-Vascular Endothelial Growth Factors from a Microsphere-Hydrogel Drug Delivery System," Current Eye Research, Jan. 2016, 8 pages.
Turturro, S. B. et al., "The effects of cross-linked thermo-responsive PNIPPAAm-based hydrogel injection on retinal function," Biomaterials, Feb. 2011, pp. 3619-3626.

(Continued)

*Primary Examiner* — Genevieve S Alley

(74) *Attorney, Agent, or Firm* — Pauley Erickson & Swanson

(57) ABSTRACT

A hydrogel delivery composition, including degradable microcapsules suspended in a degradable thermo-responsive hydrogel. The hydrogel is thermo-responsive at a physiological temperature and changes after application to a more solid state due to body temperatures. The composition includes one or more treatment agents to be released over time as the composition degrades. The composition can be varied to modify the structure and/or release of the treatment agent.

20 Claims, 10 Drawing Sheets

(56) References Cited

OTHER PUBLICATIONS

PCT International Search Report, Form PCT/ISA/210, dated Dec. 9, 2016, (2 pages).
PCT Written Opinion of the International Searching Authority, Form PCT/ISA/237, dated Dec. 9, 2016, (5 pages).

* cited by examiner

BIODEGRADABLE MICROSPHERE-HYDROGEL OCULAR DRUG DELIVERY SYSTEM

CROSS REFERENCE TO RELATED APPLICATION

This application claims the benefit of U.S. Provisional Patent Application, Ser. No. 62/232,545, filed on 25 Sep. 2015. The Provisional Patent Application is hereby incorporated by reference herein in its entirety and is made a part hereof, including but not limited to those portions which specifically appear hereinafter.

FIELD OF THE INVENTION

This invention relates generally to drug or other treatment delivery and, more particularly, to a hydrogel delivery composition and method that can deliver treatment materials in a controlled matter for an extend period of time.

BACKGROUND OF THE INVENTION

Choroidal neovascularization (CNV) secondary to age-related macular degeneration (AMD) is a leading cause of vision loss in elderly patients in developed nations. It has been demonstrated that vascular endothelial growth factor (VEGF) plays a key role in the pathophysiology of the disease. The U.S. Food and Drug Administration has approved several anti-VEGF therapeutics to treat CNV secondary to AMD, namely ranibizumab (Lucentis, Genentech, South San Francisco, Calif., USA) and aflibercept (Eylea®, Regeneron, Tarrytown, N.Y., USA). Additionally, the use of anti-VEGF therapeutics has increased for other indications such as diabetic macular edema (DME) and vein occlusion. Due to these successful outcomes, it is not surprising that there has been a paradigm shift in the use of pharmacological therapeutics over surgical techniques during the last decade to treat visually devastating diseases.

The current standard to deliver anti-VEGF therapeutics is through a monthly (or bimonthly) bolus intravitreal injection. With each injection, serious potential complications can arise including endophthalmitis, retinal detachment, intravitreal hemorrhage, and cataract. To improve upon the socio-economic impact associated with repeated injections and to further lower the risk of associated potential complications, there is a need to reduce the number and frequency of injections.

A multitude of drug delivery systems (DDSs) have been successful in controlling and extending the release of various model drugs. A common theme among these DDSs is the use of polymeric microspheres to control release. However, when microspheres are injected into the eye as independent units, they can become lodged in ocular tissues (e.g., trabecular meshwork), which may cause unintended and serious complications. Thus, there is a continuing need for improved drug delivery systems, particularly in the development of intraocular DDSs.

SUMMARY OF THE INVENTION

A general object of the invention is to provide an improved delivery system and method for delivering treatment material(s), such as on or within the eye.

The general object of the invention can be attained, at least in part, through a delivery composition including degradable microcapsules (e.g., nano- or micro-spheres or other similar microencapsulation structures) suspended in a degradable thermo-responsive hydrogel. The hydrogel is thermo-responsive in that it desirably changes its physical state from a liquid-like state at room temperature to a more solid state at body temperature (e.g., at a physiological temperature of about 32° C. to about 37° C.). The microcapsules encapsulate and release a treatment agent.

The rate of release can be controlled via the rate of degradation, which can be controlled, for example, by altering a chemical component ratio, the molecular weight of the polymer(s), surface modification, and/or manufacturing procedures. In some embodiments a non-encapsulated treatment agent can optionally be additionally dispersed within the hydrogel, and/or microcapsules having at least two different release rates can be used together.

Embodiments of this invention focus on anti-VEGF as a treatment agent, but the invention can also be used to deliver other drugs, such as ophthalmic drugs (for example, antibiotics for ocular surgery), anti-platelet-derived growth factor (anti-PDGF) agents, cells, delivery cells, a corticosteroid, enzymes, peptides, nucleic acids, or combinations thereof. The invention can, for example, reduce or eliminate patient administration of treatment after ocular surgery, such as eliminating the need to administer topical (eyedrop) antibiotics for several days. Most often, the patient compliance is low and at risk for infection.

The invention further comprehends a method of delivering a compound to an eye, including: applying to or into an eye of a mammal a composition in a first physicochemical state, wherein the composition comprises a microencapsulated treatment agent suspended in a thermo-responsive hydrogel; and the composition changing to a second physicochemical state upon administration, wherein the second physicochemical state is more solid than the first physicochemical state and degradable to release the microencapsulated treatment agent. The applied microcapsules release the bioactive treatment agent over time after application.

The method can be used with any composition described herein. In embodiments of this invention, the degradation can be controlled by the type of and/or amount of cross-linking within the composition, thereby controlling the release the microencapsulated treatment agent. Using more than one microencapsulated treatment agent, such as different microencapsulations for a same agent type, and/or also placing non-encapsulated agent in the hydrogel itself, can also or further be used to provide a desired release.

Compositions of this invention can be applied by any suitable manner, desirably in a first physicochemical state, such as by intravitreal injection, by periocular or transcleral injection, by topical application including scleral structures, by intracameral application, by suprachoroidal application, within ocular implants, or combinations thereof. Injections can be made by small gauge needle (e.g., 20 gauge to 33 gauge) or by microcatheter.

Other objects and advantages will be apparent to those skilled in the art from the following detailed description and examples taken in conjunction with the appended claims and drawings.

DESCRIPTION OF THE INVENTION

Figure 1:
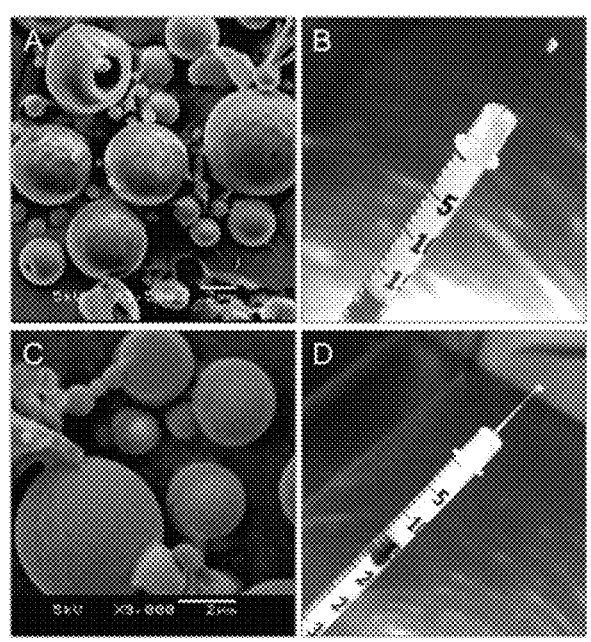
FIG. 1 shows: A) a representative SEM image of ranibizumab-loaded microspheres (scale bar: 2 μm); B) a ranibizumab-loaded DDS in a 28G needle; C) a representative SEM image of aflibercept-loaded microspheres (scale bar: 2 μm); and D) an aflibercept-loaded DDS in a 28G needle at room temperature.

The present invention provides a hydrogel delivery composition and method that can delivery treatment materials (e.g., drugs, etc.) in a controlled matter for an extend period of time. Encapsulating and releasing, for example, a bioactive drug for a long period of time is a difficult task. Many laboratories have tried to do this with limited success.

The composition of embodiments of this invention combines both hydrogel and microcapsules for treatment. Degradable microcapsules are suspended in a degradable thermo-responsive hydrogel. The hydrogel is thermo-responsive at a physiological temperature of about 32° C. to about 37° C., such as to change, via crosslinking, from a liquid-like state at room temperature to a more solid state at body temperature. Exemplary hydrogel materials include poly(N-isopropylacrylamide), poly(latic acid), polysaccharide chitin, alginate, polyethylene glycol (PEG) and/or diacrylate (DA), or combinations or copolymers thereof. Exemplary copolymers include block copolymers PEG-PLLA-DA or PLA-PEG-PLA.

The thermo-responsive hydrogels of this invention provide an injectable platform material that solidifies once injected into position. Small gauge needles, e.g., about 20 to 33 gauge, and preferably about 25 to 27 gauge, such as used in conventional intravitreal injection treatment, can be used to deliver the composition of this invention. This can be a significant benefit as the injections can occur in doctor's office rather than in an operating room. The thermo-responsive hydrogels of this invention are injected in the "liquid-like" form and "solidify" to a gel material at body temperature. The transition time can be controlled, so that the hydrogel can be used for various applications.

The hydrogels are desirably biodegradable, and can be either partially or fully biodegradable. The duration of degradation can also be controlled. In embodiments of this invention, the degradation rate is controlled by the type and/or amount of crosslinker contained in the 'liquid' form of the composition. In another embodiment, the degradation rate is modified by using different concentrations of and/or chain transfer agents (e.g., glutathione) with poly(N-isopropylacrylamide).

In embodiments of this invention, the thermo-responsive hydrogel is used to suspend or otherwise entrap microcapsules, e.g., nano- or microspheres, for easier delivery as well as localized delivery of the microcapsules. Microcapsules generally will not stay in the eye when injected alone. Studies have shown that microcapsules will clear within about fifty days in normal eyes and within fourteen days in vitrectomized eyes. Injecting microcapsules alone to deliver a long-term drug treatment will not work. Another concern is that "free floating" microcapsules (if they are big enough) can interfere with visual function, in that a patient may 'see' microcapsules floating and interfere with vision. By incorporating microcapsules into hydrogel according to this invention, the hydrogel structure 'keeps' the microcapsules in place to provide longer-term delivery. Keeping microcapsules in the hydrogel also avoids interfering with the central visual pathway (visual perception).

The microcapsules are also desirably biodegradable, and can be either partially or fully biodegradable. The duration of degradation and/or release can also be controlled. The degradation time and thus release rate can be controlled, for example, through changing the polymer ratio, modifying the molecular weight of polymer(s), surface modification, and/or manufacture procedure. Currently preferred biodegradable microcapsules are based on poly(lactic-co-glycolic acid) (PLGA). Exemplary microcapsules according to this invention are formed using any suitable microencapsulation process from poly(lactic-co-glycolic acid), poly(latic acid) (PLA), polysaccharide chitin, alginate (polysaccharide), or combinations or copolymers thereof. Exemplary copolymers include, without limitation, PLGA-chitin and block copolymers with polyethylene glycol (PEG) and/or diacrylate (DA), such as PLGA-PEG, PEG-PLLA-DA, PEG-PLGA-PEG, and PLGA-PEG-PLGA.

The invention includes a microencapsulated treatment agent suspended in a thermo-responsive hydrogel, for the purpose of delivering the treatment agent to a delivery site. The microencapsulated treatment agent-in-hydrogel composition of this invention changes to a second, more solid physicochemical state upon administration, and then degrades to release the treatment agent. The hydrogel keeps the microcapsule in place (localized to delivery site) and prevents free movement of microcapsule in and/or around the eye. The hydrogel can also act as another release barrier and prolong the release time. The applied microcapsules release the bioactive treatment agent over time after application. Any suitable treatment agent can be encapsulated by any suitable encapsulation method. Exemplary treatment agents include, without limitation, drugs, antibiotics (e.g., vancomycin, gentamicin), corticosteroids (e.g., dexamethasone, triamcinolone acetonide), anti-VEGF (e.g., pegaptanib, vevacizumab, ranibizumab, aflibercept, convercept), anti-PDGF, peptides, enzymes, biological agents (e.g., nucleic acids: DNA, RNA), various stem or other cells, or combinations thereof.

Treatment agent(s) can release from the microcapsule only, from both the microcapsule and the hydrogel, from combinations of different size microcapsules, from both different size of microcapsules and hydrogel, etc. Combination of treatment agents can be released (e.g., anti-VEGF and anti-PDGF, or combination of two different antibiotics) from the same or different microcapsules and/or from the microcapsule and the hydrogel. These variations allow for different release rates and/or treatments. In one embodiment of this invention, the thermo-responsive hydrogel is used to deliver a same or different agent in addition to the microspheres. The hydrogel itself can be, for example, drug-loaded and the release can be controlled; hence, providing another option to deliver agents in conjunction with microcapsules. This can be ideal in a long-term delivery. For example, hydrogels can deliver "loading" doses of drugs and the microspheres deliver "maintenance" doses.

Microcapsule-hydrogel platforms of this invention can provide long-term release of anti-VEGF, such as a controlled release of anti-VEGF for over 6 months. Both in vitro and in vivo studies have shown that released anti-VEGF agents are active for the duration. This means that anti-VEGF can be safely stored in the drug delivery platform of this invention and the released drug has a positive effect clinically. Both modified microcapsule fabrication steps (adding protective agent for treatment agent) and using hydrogel provided both extended release and bioactivity of the drug.

The delivery system can encapsulate various ocular drugs. The platform of this invention can replace monthly conventional intravitreal injection treatment. Another novel application is to release multiple drugs at the same time. By encapsulating different drugs (or the same drug with different dosages), drugs can be controlled and released at different rates. As an example, clinically, there is growing evidence that dual treatment of anti-VEGF and anti-PDGF (both delivered conventionally intravitreal injection method) may be beneficial over monotherapy of anti-VEGF. The platform of this invention can be utilized to release both anti-VEGF and anti-PDGF for an extended period of time.

As discussed above the composition of this invention can be injected, and can also be used topically or in other medical procedures/devices. As an example, an illuminated microcatheter (such as iTrack microcatheter, iScience Interventional) can be used to deliver various agents (encapsulated drugs or cells) into the suprachoridal space. Microcatheter injection has not typically been successful due to a backflush of drug after the injection. The biodegradable thermos-responsive composition of this invention will help keep the treatment agent in place (due to the change from liquid-like to solid-gel) after injection.

The composition of this invention can also be injected around the eye globe to act as a temporary scleral structure, such as a scleral buckle for retinal detachment treatment. Currently, only permanent scleral buckles (made out of surgical sponge or plastic) are used even though the original intent of buckle use was a temporary procedure. The composition can be injected directly into the globe to provide structural support (like a scleral buckle). Because the composition is biodegradable, there will be no need to remove the hydrogel. Furthermore, it can be combined with agents (e.g., antibiotic) to prevent any post-procedure infection. Since it will be simple injection, the procedure should be minimally invasive. Because the polymer composition can be controlled, the hydrogel can be made more firm to give sufficient structural support.

The composition can be used in existing or future medical devices. For example, the composition can be filled inside of ocular implants such as a Port Delivery System (PDS, developed by ForSight Vision4 and licensed by Genentech), which is a refillable, non-biodegradable implant (surgical procedure), or other implant reservoirs. Patients typically need 4-5 refills over 12 months. Because the composition of this invention can release for over 6 months, a combination system can extend treatment.

The present invention is described in further detail in connection with the following examples which illustrate or simulate various aspects involved in the practice of the invention. It is to be understood that all changes that come within the spirit of the invention are desired to be protected and thus the invention is not to be construed as limited by these examples.

EXAMPLES

A drug delivery system (DDS) was prepared, composed of biodegradable poly(lactic-co-glycolic acid) (PLGA) microspheres suspended within a thermo-responsive, injectable poly(N-isopropylacrylamide) (PNIPAAm)-based hydrogel. In the initial development of this DDS, ovalbumin was used as a model protein to demonstrate controlled and extended release for approximately 200 days. By suspending the microspheres within hydrogel, the initial burst (IB) was greatly reduced and release was extended by ~30% compared to microspheres alone. Several excipients were incorporated into the DDS to protect against the acidic degradation products of PLGA as well as to protect the protein (drug) during preparation, storage, and release. The objective of this work was to demonstrate the capability of the microsphere-hydrogel DDS of this invention to release either ranibizumab or aflibercept in a controlled and extended manner and to determine whether the drugs remain bioactive throughout release.

Ranibizumab and aflibercept were radiolabeled (to determine release rate) with iodine-125 using iodination beads (Pierce, Rockford, Ill., USA) and then dialyzed against double-deionized water (ddH$_2$O) using a dialysis cassette (MWCO 2 kDa, Pierce) to remove unbound, free iodine. Labeled proteins were lyophilized, weighed, and dissolved in 1× phosphate-buffered saline (PBS, pH 7.4) to create stock solutions of 10 mg/mL for each protein, which were stored at −80° C.

All subsequent chemicals were purchased from Sigma-Aldrich (St. Louis, Mo., USA). Each anti-VEGF was incorporated into PLGA microspheres using a modified double-emulsion, solvent evaporation technique described in Osswald C. R. et al., Controlled and Extended Release of a Model Protein from a Microsphere-Hydrogel Drug Delivery System, Ann Biomed Eng., Apr. 3, 2015. Briefly, each protocol contained the same excipients in the inner aqueous ($w_1$) and oil (o) phases and each protocol was made in triplicate. In the $w_1$ phase, 12.5 mg bovine serum albumin (BSA), 10 mg PEG (molecular weight, MW, 8 kDa) (added to 'protect' the agent), and 2.5 mg sucrose were dissolved in 100 μL of stock anti-VEGF solution. In the o phase, 125 mg PLGA 75:25 (4-15 kDa, acid terminated) and 3.75 mg Mg(OH)$_2$ (also added to 'protect' the agent) were dissolved in 0.5 mL dichloromethane.

The primary water-in-oil emulsion (wt/o) was created by vortex at 3200 rpm for 90 s (Fisher Scientific Analog Vortex Mixer; 120 V; speed 10×). The $w_1$/o emulsion was immediately added to the outer aqueous phase ($w_2$) containing 10% (w/v) polyvinyl alcohol (PVA). The secondary (water-in-oil)-in-water emulsion ($w_1$/o/$w_2$) was created by vortex at 2200 rpm (speed 5×) for 90 s. The $w_1$/o/$w_2$ emulsion was then added to 75 mL of 0.2% PVA followed by solvent evaporation on a stir plate (400 rpm for 3 h). Microspheres were harvested by centrifugation (2000 ref), washed three times in ddH2O, lyophilized to a dry powder, and stored at 4° C.

For each anti-VEGF agent, encapsulation efficiency (EE) was determined from the radioactivity measured using a gamma counter (Cobra-II Auto-Gamma, Packard Instrument Co., Meriden, Conn.) before and after microsphere preparation. EE was defined as the percent-drug within the microspheres relative to the theoretical loading amount.

To measure microsphere diameter, microspheres were fabricated as described above with non-radiolabeled drug. A sample was suspended in ddH$_2$O and imaged with a microscope (×20 objective, Carl Zeiss, Germany). Images of microspheres (n=135) were analyzed using ImageJ (developed by Wayne Rasband, National Institutes of Health, Bethesda, Md.) to measure the diameter.

Morphology of the microspheres was also examined by scanning electron microscopy (SEM). Dry microspheres were mounted on double-faced adhesive carbon tape on metal stubs, sputter-coated with gold (E5000M S.E.M. Coater, Polaron Equipment Ltd., UK), and further analyzed in a scanning electron microscope (JSM-5900LV, Jeol USA, Inc., Peabody, Mass.).

PNIPAAm-PEG-diacrylate (DA) hydrogels were synthesized using a method described in Osswald C. R. et al. Hydrogels were made in triplicate and prepared by dissolving PEG-DA (MW 575 Da, 2 mM), N-tert-butylacrylamide (47 mM), and ammonium persulfate (13 mM) in 1× Dulbecco's PBS (with CaCl$_2$ and MgCl$_2$). Then, NIPAAm (350 mM) was added to create the hydrogel precursor. Microspheres (15 mg) were suspended in 1 mL of precursor in a 2 cc microcentrifuge tube and kept on ice. Polymerization of the hydrogel was initiated by adding N,N,N',N'-Tetramethylethylenediamine (168 mM). After polymerization, hydrogels were collected and washed three times in ddH2O.

Release of anti-VEGF agents was determined using a separation method also described in Osswald C. R. et al. Briefly, 15 mg of microspheres and 1 mL, of the DDS (15 mg microspheres in 1 mL hydrogel) were suspended in 1.5 mL of 1×PBS to ensure detectable levels of anti-VEGF concentration throughout release. Release profiles were conducted at 37° C. under mild agitation and at predetermined intervals, 1 mL of supernatant was removed after a brief centrifugation and replaced with an equal volume of fresh buffer. Supernatants were read using a gamma counter (Packard). Cumulative release was calculated as a percent of encapsulated drug and was considered complete when the microspheres had completely degraded based on visual inspection. The IB was defined as drug released within the first 24 hours.

For the bioactivity studies, non-radiolabeled release samples were kept at −80° C. until bioactivity testing. To determine bioactivity, human umbilical vascular endothelial cells (HUVECs) were cultured, trypsinized, and seeded in 96-well plates at 5000 cells per well in growth medium (EGM-2, Lonza Inc., Allendale, N.J., USA). After the cells had grown to ~80% confluence (48 hr), cell growth was arrested by washing the plates twice with 1×PBS and then adding 50 μl of basal growth media (EBM-2, Lonza) to each well. To achieve VEGF-induced proliferation, 25 μL of 10 ng/mL exogenous VEGF (taken from a BulletKit, Lonza) and 25 μL of a release sample of anti-VEGF were then added to each well. Each release sample was done in duplicate for a total of six samples per time point (microspheres alone and DDS made in triplicate). A solution containing a tetrazolium compound [3-(4,5-dimethylthiazol-2-yl)-5-(3-carboxymethoxyphenyl)-2-(4-sulfophenyl)-2H-tetrazolium, inner salt; MTS] and an electron coupling reagent (phenazine ethosulfate) (MTS assay, CellTiter 96® AQ$_{ueous}$ One Solution Reagent; Promega, Madison, Wis., USA) was used according to the manufacturer's protocol to determine cell proliferation and cytotoxicity after two days of exposure to the release samples. In the MTS assay, cell proliferation is proportional to the optical density (OD) of the sample when read using a spectrophotometer at 490 nm from 1-4 hours. Cell proliferation was normalized relative to those wells receiving only exogenous 10 ng/mL VEGF (negative control). Positive controls consisted of 25 μL of a clinical dose of drug (10 mg/mL ranibizumab or 40 mg/mL aflibercept) added to wells containing 10 ng/mL VEGF.

All values are reported as mean±standard error and in all graphs, error bars represent standard error. Significant differences in microsphere diameter, EE, and IB were determined using Student's t-test. For the bioactivity studies, significance at each time point was determined using Student's t-test. Significance between the test conditions was determined using one-way ANOVA followed by the Holm-Sidak test. Unless otherwise noted, significance represents $p<0.05$.

PLGA microspheres loaded with either ranibizumab or aflibercept were successfully created and suspended within a thermo-responsive PNIPAAm-based hydrogel. Representative images of ranibizumab- and aflibercept-loaded microspheres can be seen in FIGS. 1A and 1C, respectively, with microspheres appearing smooth and non-porous. After the microspheres were suspended within the hydrogel, the DDS remained injectable through a 28 G needle at room temperature (22° C.; FIGS. 1B and 1D). Particle size and EE for ranibizumab- and aflibercept-loaded microspheres alone and suspended in hydrogel can be seen in Table 1. The EE was not significantly different for either drug when comparing microspheres alone to those in hydrogel (p>0.65); however, ranibizumab-loaded microspheres had twice the EE compared to aflibercept-loaded microspheres.

TABLE 1

Characteristics of release for both ranibizumab- and aflibercept-loaded microspheres and the same suspended in hydrogel.

| | | Diameter (μm) | Encapsulation Efficiency Percent (%) | Encapsulation Efficiency Weight (μg) | Initial Burst Percent (%) | Initial Burst Weight (μg) |
|---|---|---|---|---|---|---|
| Ranibizumab | Alone | 7.5 ± 0.4 | 91.3 ± 2.5 | 149.6 ± 3.7 | 50.3 ± 2.1 | 113.2 ± 4.7 |
| | in hydrogel | | 89.5 ± 2.8 | 106.2 ± 3.0 | 21.0 ± 2.0 | 22.2 ± 2.2 |
| Aflibercept | Alone | 8.0 ± 0.3 | 44.8 ± 2.0 | 169.8 ± 3.4 | 83.3 ± 2.1 | 65.3 ± 0.7 |
| | in hydrogel | | 44.6 ± 1.4 | 65.4 ± 0.9 | 20.1 ± 0.8 | 31.1 ± 0.5 |

The hydrogel provided a significant reduction in the IB for both anti-VEGF drugs. For ranibizumab, the IB was reduced by 58% (p=0.0003) and for aflibercept, the IB was reduced by 76% (p=0.0002) (Table 1). Beyond the first week of release, release from microspheres alone for both ranibizumab and aflibercept was minimal (FIGS. 2A and 3A). This release phenomenon is often seen in protein-loaded microsphere. It results from the majority of protein being surface-bound, which quickly diffuses away. Thus, there is minimal protein entrapped within the bulk of the microsphere, which precludes release at later time points from microspheres alone.

In contrast, suspending microspheres in hydrogel resulted in steady release of 0.153 μg/day of ranibizumab (FIG. 2B) and 0.065 μg/day of aflibercept (FIG. 3B) from Days 7-196. Thus, the hydrogel provides sufficient resistance to the diffusion of surface-bound anti-VEGF, which yields controlled release throughout. Additionally, both ranibizumab- and aflibercept-loaded microspheres completely degraded after 154 days, whereas suspending the microspheres in hydrogel extended the release of both drugs by 27.2% to 196 days.

Figure 2:
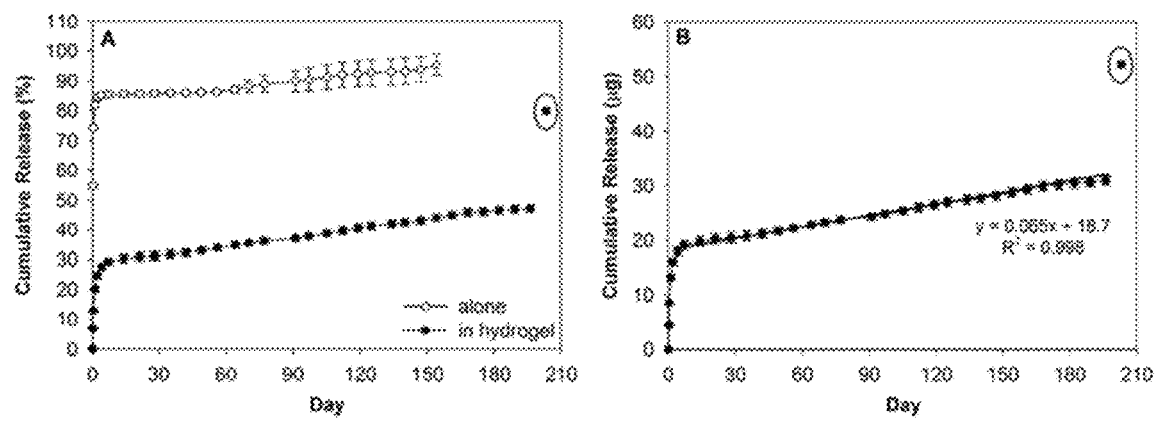
FIG. 2 includes graphs of: A) cumulative percent-release of ranibizumab from microspheres ("alone") and microspheres suspended in hydrogel ("in hydrogel"), where the microspheres in hydrogel had a significantly lower IB and a steadier, extended release; and B) cumulative drug-release from microspheres in hydrogel, where after Day 7, 0.153 µg/day of ranibizumab was released and an additional, 25.1±12.1% (27.3 µg) of encapsulated drug remained entrapped in the hydrogel after complete degradation of the microspheres (circled). Error bars represent standard error (n=3).
Figure 3:
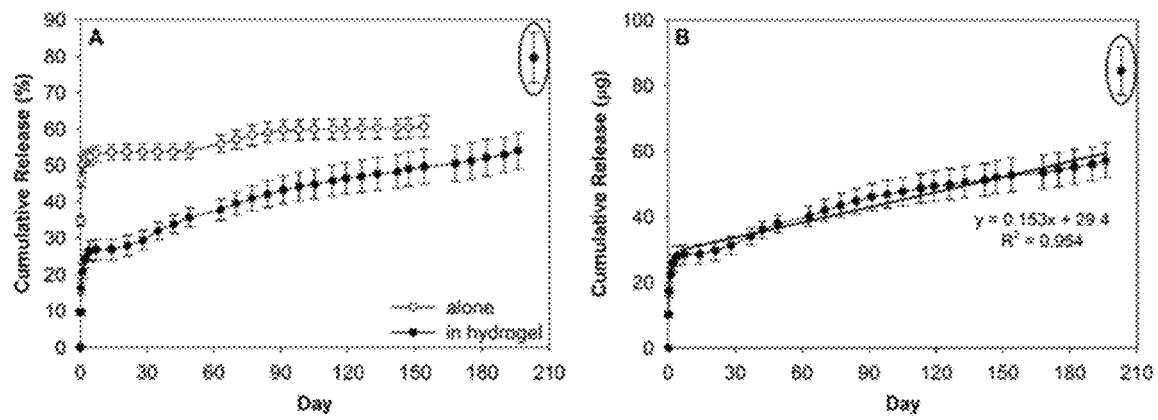
FIG. 3 includes graphs of: A) cumulative percent-release of aflibercept from microspheres ("alone") and the effect of suspending microspheres in hydrogel ("in hydrogel"), where flibercept-loaded microspheres suspended in hydrogel had a significantly lower IB and a steadier, extended release; and B) cumulative drug-release from microspheres in hydrogel, where after the first week, 0.065 µg/day of aflibercept was released, and an additional, 32.7±1.1% (21.4 µg) of encapsulated drug remained entrapped in the hydrogel after complete degradation of the microspheres (circled in red). Error bars represent standard error (n=3).

Hydrogels were checked for translucency beginning on Day 154 (time at which microspheres alone had completely degraded but not microspheres in hydrogel) to determine whether the microspheres had degraded. This was done by lowering the temperature of the hydrogel from 37° C. to 22° C. and determining, by visual inspection, whether microspheres remained within the hydrogel. The hydrogels returned to their translucent state at 203 days; thus, degradation of the microspheres was determined to be complete by 196 days. (11) An additional 25.1±12.1% (27.3 μg) of ranibizumab and 32.7±1.1% (21.4 μg) of aflibercept remained entrapped in the hydrogel after complete degradation of the microspheres (FIGS. 2 and 3, respectively; circled in red).

Figure 4:
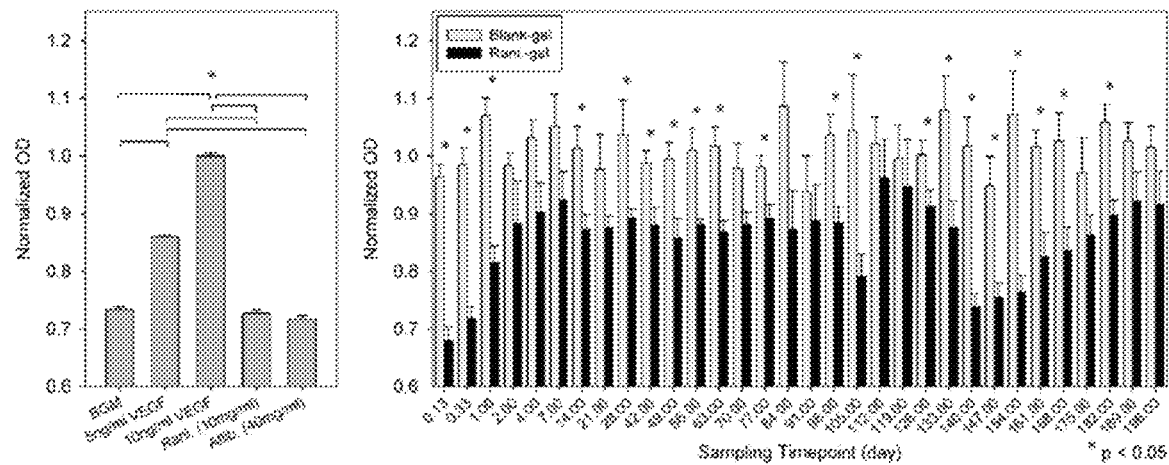
FIG. 4 shows bioactivity of the ranibizumab-loaded DDS ("Rani.-gel"). Significant bioactivity ($p<0.05$) is seen throughout release of ranibizumab compared to the drug-free DDS ("Blank-gel"; right). Error bars represent standard error (n=16, left; n=6, right).
Figure 5:
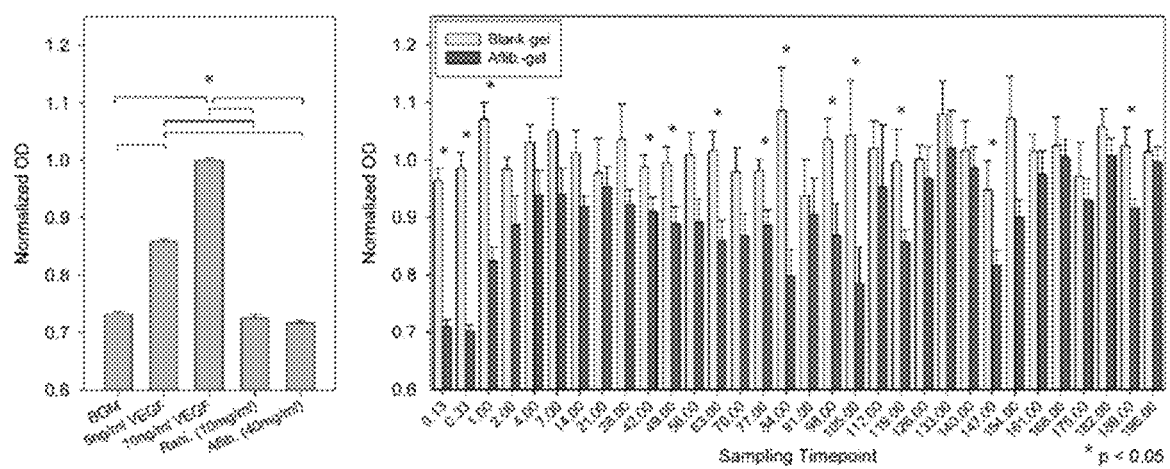
FIG. 5 shows bioactivity of the aflibercept-loaded DDS ("Aflib.-gel"). Significant bioactivity ($p<0.05$) is seen throughout release of aflibercept compared to the drug-free DDS ("Blank-gel"; right). Error bars represent standard error (n=16, left; n=6, right).

Bioactivity was maintained throughout release. A proportional increase in HUVEC proliferation was observed with increased VEGF concentration (FIGS. 4 and 5, left panels). Positive controls (clinical dose of each drug) significantly inhibited VEGF-induced proliferation of HUVECs (p<0.0007) and no difference was seen between positive controls and basal growth medium (BGM, p>0.92).

For both drugs, significant inhibition of VEGF-induced HUVEC proliferation was observed during the IB (p<0.05). At all subsequent time points, HUVEC proliferation was less for the drug-loaded DDS compared to the non-loaded DDS counterparts (labeled as "Blank-gel" in FIGS. 4 and 5). For both the ranibizumab- (FIG. 4, right panel) and aflibercept-loaded DDS (FIG. 5, right panel), significant inhibition of HUVEC proliferation was observed at many time points throughout release, including later release time points ($p<0.05$). Additionally, both drugs remain bioactive throughout release as indicated by a lower normalized OD for drug-treated HUVECs compared to control at every time point (FIGS. 4 and 5, right panes). However, at various time points, an insufficient amount of bioactive anti-VEGF was available to significantly inhibit HUVEC proliferation ($p>0.05$).

Controlled and extended release of bioactive ranibizumab and aflibercept was achieved for ~200 days by encapsulating these drugs in PLGA 75:25 microspheres suspended in a PNIPAAm-based hydrogel. Compared to microspheres alone, the hydrogel significantly lowered the IB of both drugs and extended the release of each by almost a third. Additionally, the hydrogel allowed for significant bioactivity of both drugs to be maintained throughout. If these results are verified in vivo, bioactive and controlled release for nearly 200 days is a significant step towards replacing the current monthly/bimonthly treatment regimens approved for these drugs.

Interestingly, ranibizumab-loaded microspheres had twice the EE of aflibercept-loaded microspheres even though the theoretical loading was the same and the drugs were treated identically in the fabrication of the microspheres. A likely cause for this is the difference in MW between the drugs. It has been shown across a variety of fabrication techniques, including the double-emulsion technique used in this study, that smaller proteins tend to have a higher EE. Larger proteins tend to remain surface-bound at the polymer-water interface, as was evidenced by the significantly higher IB for aflibercept (MW 115 kDa) compared to ranibizumab (MW 48 kDa). Additionally, charge and tensioactive properties of the proteins may have contributed to the differences seen in EE.

Suspending microspheres within the thermo-responsive hydrogel according to this invention significantly reduced the IB by 58% and 76% for ranibizumab and aflibercept, respectively. The reduction in IB may be attributed to the fabrication of hydrogel (e.g., surface diffusion of drug into hydrogel precursor prior to gelation) and the hydrogel acting as a diffusion barrier. A larger protein would see a greater diffusion barrier; thus, it was anticipated and shown that the reduction in IB was greater for aflibercept than ranibizumab. Importantly, suspending the microspheres within the thermo-responsive hydrogel yielded steadier and more controlled release compared to microspheres alone. This microsphere-hydrogel DDS approach has been shown previously to provide better control and extended release compared to microspheres alone. Thus, the DDS of this invention has two potential benefits for the treatment of posterior segment eye diseases: it would prevent the independent movement of microspheres within the eye as well as provide prolonged and controlled release of anti-VEGFs.

Figure 6:
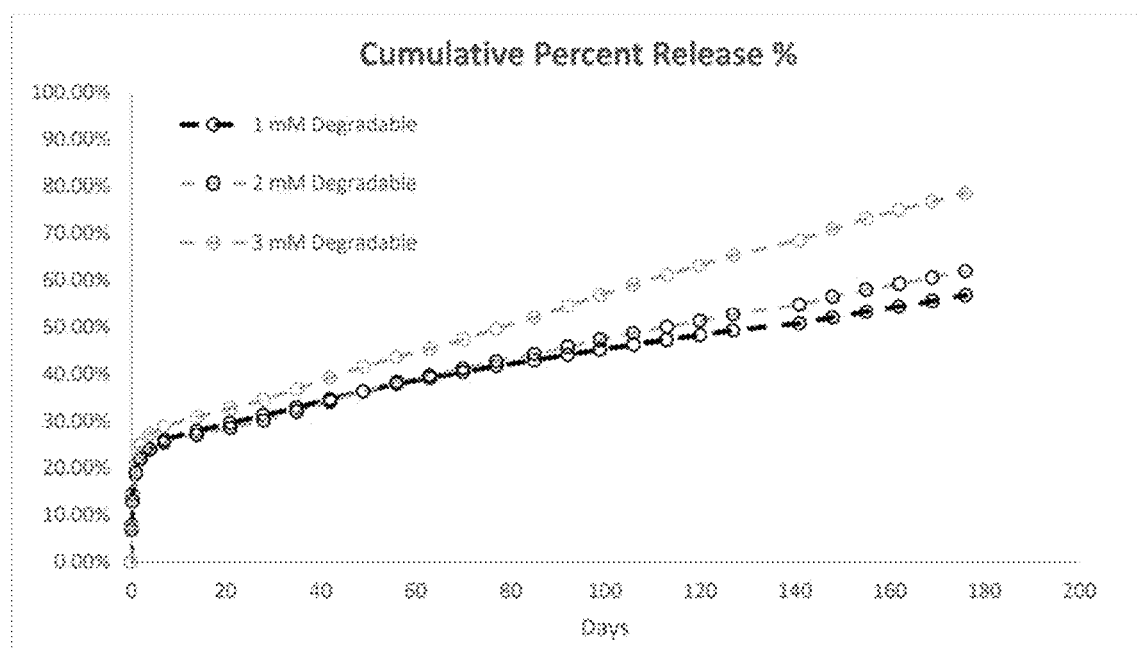
FIG. 6 shows release of ranibizumab from biodegradable microspheres and biodegradable thermo-responsive hydrogel, where different amounts of crosslinker were used to change the degradation rate.

For both anti-VEGFs, a residual amount of drug was observed trapped in the hydrogel at the end of the study (final time point, FIGS. 2 and 3). In a study by one of the inventors using PNIPAAm-based hydrogel to encapsulate BSA and immunoglobulin G (IgG), a similar entrapment was observed. Aflibercept had a higher residual entrapment (32.7±1.1%) than the smaller ranibizumab (25.1±12.1%), which had a higher residual entrapment than the smaller ovalbumin (45 kDa) observed in our prior study (8.01±0.76%). Non-degradable hydrogels were used intentionally in this study to simplify the experimental factors and focus on the release of ranibizumab and aflibercept. The issue of entrapped drug using the hydrogel can be mediated by utilizing fully biodegradable hydrogels. Hydrogels with varying lengths of degradation can have an effect on release from microspheres. For example, FIG. 6 summarizes data from an experiment (though 180 days) showing release of ranibizumab from biodegradable microspheres and a biodegradable thermo-responsive hydrogel. Different amounts of crosslinker (PLLA-PEG-DA) were used to change the degradation rate.

Including the residual entrapped drug, incomplete release (that is, not achieving 100% cumulative release) was still observed. This phenomenon is frequently reported in many protein-loaded PLGA microsphere delivery platforms and may be due to protein instability. Protein aggregation and non-specific protein adsorption are typically the leading causes of incomplete release and differences in the isoelectric point (pI) of each drug may be to blame. At pH lower than the pI, proteins carry a net positive charge and vice versa. In a previous study using ovalbumin, complete release was observed. The pI of ovalbumin is ~4.6, whereas monoclonal antibodies (e.g., ranibizumab) typically have a pI of ~8. Thus, performing these experiments at physiological pH (7.4) may have influenced the release due to possible charge interactions between the drugs, PLGA, and hydrogel.

Significant bioactivity is seen during late release time points (i.e., beyond 100 days), a timeframe well beyond the IB where a large amount of drug was released. In our initial characterization of this DDS with ovalbumin, a large second burst occurred after Day 70 and release beyond the second burst occurred at a greater rate than prior to the second burst. The IB can be readily explained by diffusion of drug located near the particle surface through short diffusion pathways. As PLGA swells and degrades, the pores become large enough to allow for the release of entrapped protein, which can lead to a second burst. Although a large second burst was not observed in this study for either anti-VEGF-loaded DDS, it is likely that at these later time points, even though the amount of protein was small, the protein was likely intact and thus as bioactive as during the IB. Proteins at interfaces (e.g., surface-bound protein during the IB) tend to easily denature whereas proteins entrapped within the microsphere (i.e., release at later time points) tend to remain intact and bioactive.

The release of bioactive anti-VEGF for over six months is a significant step toward eliminating monthly or bimonthly bolus injections of drugs needed to treat many posterior segment eye diseases. The extended and controlled release of anti-VEGF agents that the DDS of this invention demonstrates may be a significant advancement in the delivery of protein therapeutics to the eye once validated in vivo. The DDS of this invention has the potential to improve upon the socio-economic impact associated with recurrent injections and to lower the risk for associated potential complications.

To further validate the potential of the DDS of this invention to treat posterior segment eye diseases, the in vivo efficacy of the DDS was determined using a rat model of CNV. Animal models of CNV fall into three categories: laser and light induced, surgically induced, and transgenic and knockout mouse models. These models have a common beginning: a break or defect in Bruch's membrane. Development of CNV is a dynamic process with initiation, maintenance, and involution stages. Currently, the most common way to induce CNV in animals is through the use of laser photocoagulation as it is relatively simple to create, is inexpensive, and is reproducible.

In rats, approximately 75% of lesions are vascularized within the first week following CNV induction; after ten days, CNV is fully developed and remains so for at least 35 days after induction. Additionally, it has been found that the highest rate of blood vessel growth (3-10 days after induction) correlates with the peak expression of VEGF and its receptor. Furthermore, using vascular cast images it has been shown that features of laser-induced CNV in rats were similar at one and three months but that CNV had atrophied by six months. Accordingly, lesions should be monitored at least weekly in the beginning of CNV development, with the assumption that CNV is not fully developed until two weeks post-induction and lesions may begin to atrophy after three months.

Several methods exist to quantify CNV lesion growth. Often, a four-tier grading scale is used ranging from no leakage to severe leakage/hyperfluorescence, where FA images are analyzed by trained retinal specialists, averaged, and compared. However, this method remains somewhat subjective and can be influenced by image properties (e.g., brightness and contrast). More complex and objective methods involve flat-mount preparations, immunohistochemistry with serial reproductions, and OCT. However, these complex methods can quickly become quite expensive and time consuming. To address the issues of objectivity, ease of use, and cost-effectiveness, a novel technique was developed based on FA images and Otsu thresholding to monitor CNV lesion growth.

Figure 7:
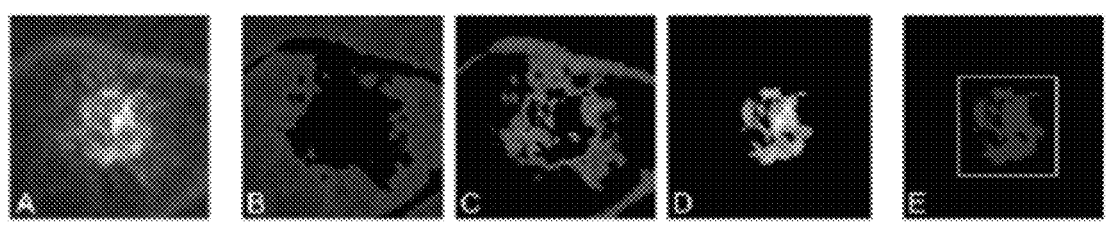
FIG. 7 shows an example of a CNV lesion area quantification technique: A) the original image opened in ImageJ and three levels are selected. AfterMOT, three images are produced: B) Region 0 (background), C) Region 1 (diffuse leakage), and D) Region 2 (CNV). With Region 2 selected, the threshold is adjusted to include all pixels within the image. The lesion is outlined (square in E) and the number of pixels within the lesion is measured, which is then converted into an area.

Otsu thresholding allows for the automatic reduction of a grayscale image into a binary foreground/background image such that an optimum threshold separating the two classes maximizes the inter-class variance of pixel intensity. This can be extended to separate intermediate levels and has been implemented as a plug-in for the open-source software ImageJ (NIH). To quantify CNV areas, three levels (or "regions") are defined: background, diffuse leakage, and CNV (FIG. 7). When determining CNV areas, the CNV lesion is outlined with blood vessels avoided. The lesion area is measured in pixels, which can then be converted into area using a scaling factor.

The ability of controlled and extended release of anti-VEGF from the DDS to inhibit CNV lesion growth was tested and compared to that of a corresponding bolus injection of anti-VEGF. Six treatment groups were observed: non-treatment, drug-free DDS, ranibizumab-loaded DDS, ranibizumab bolus, aflibercept-loaded DDS, and aflibercept bolus. Along with determining CNV areas, ocular health was monitored to demonstrate that the DDS was biocompatible and well-tolerated in vivo. It was hypothesized that controlled and extended release of anti-VEGF from the DDS will more effectively treats CNV than a bolus injection and that ocular health will be maintained throughout the study.

All animal procedures were in accordance with protocols approved by the Institutional Animal Care and Use Committee at the Illinois Institute of Technology, and with the principles embodied in the statement on the use of animals in ophthalmic and vision research adopted by the Association for Research in Vision and Ophthalmology. Long-Evans male rats (1-3 months, 300-350 g) were purchased from Harlan Laboratories (Indianapolis, Ind., USA). Animals were anesthetized using 80 mg/kg of ketamine hydrochloride (Fort Dodge Animal Health, Fort Dodge, Iowa, USA) and 10 mg/kg xylazine (AnaSed® Injection, Akorn, Inc., Decatur, Ill., USA) via intraperitoneal (IP) injection. Proparacaine drops (Bausch and Lomb, Rochester, N.Y., USA) were used to anesthetize the corneas throughout the procedure and pupils were dilated using phenylephrine (Bausch and Lomb) and atropine drops (Bausch and Lomb). Heart rate and blood oxygen saturation were monitored with a PulseOximeter (8500AV; Nonin Medical Inc., Plymouth, Minn., USA). Animals were placed on a custom-built heated stage and monitored to maintain a core body temperature of 37° C.

Non-radiolabelled, ranibizumab-, and aflibercept-loaded microspheres were prepared. Fifteen (15) mg of microspheres were put in a 2 cc microcentrifuge tube and placed under UV light for 30 min to sterilize. Under sterile conditions, the hydrogel precursor and initiator were sterile-filtered using 13 mm syringe filter (0.22 µm, Fisherbrand, Thermo Fisher Scientific, Waltham, Mass., USA). One (1) mL of hydrogel precursor was added to the microspheres and the tube was inverted several times to suspend the microspheres. The initiator was then added and free radical polymerization occurred on ice for 30 min. Hydrogels were washed three times in sterile PBS, loaded into 0.5 cc U-100 insulin syringes (28G½; Becton Dickinson & Co., Franklin Lakes, N.J., USA), and stored at 4° C.

Laser photocoagulation was performed using an argon-green laser (AKC-8000, NIDEK, Inc., Fremont, Calif., USA) attached to a slit lamp with a laser power of 400 mW, duration of 100 ms, and spot diameter of 50 µm. Using a 90-diopter lens, the posterior pole of the eye was viewed and the laser beam focused on the retina. Five to six lesions per eye were induced two to three disc diameters from, and centered on, the optic disc. Laser-induced disruption of Bruch's membrane was identified by the appearance of a bubble at the site of photocoagulation. Laser spots that did not result in the formation of a bubble were excluded from study.

Animals were separated into six groups to determine the ability of the DDS of this invention to treat CNV. For analysis purposes, lesions were considered independent within each treatment group and each group contained two rats for a total of four eyes and up to 24 lesions per treatment group. The treatment groups were as follows: 1) control group, which did not receive any treatment or injection after laser induction ("non-treatment"); 2) non-loaded DDS ("Blank-gel"); 3) ranibizumab-loaded DDS ("Rani.-gel"); a single bolus injection of ranibizumab at clinical dose (10 mg/mL, "Rani."); a single bolus injection of aflibercept-loaded DDS ("Aflib.-gel"); aflibercept at clinical dose (40 mg/mL, "Aflib."). All IVT injections were 5 µL and performed immediately after CNV induction.

The corneal electroretinogram (ERG) is a non-invasive measurement that represents the overall electrical activity of the retina in response to a stimulus flash. It is routinely used to assess retinal cellular activity and in toxicology studies. Each component of the ERG can be used to assess different retinal cell types and any alterations in the function of the retina due to the DDS would appear as changes in amplitude or sensitivity of various ERG components. Under scotopic conditions, the ERG has two important components: the a-wave and b-wave. The rising edge of the negative a-wave is generated by the photoreceptors in the outer retina; the positive b-wave is generated primarily by the bipolar cells and/or Müller cells. Another component of the ERG is the c-wave, which originates in the RPE and can be used to assess the functional integrity of the photoreceptors, the RPE cells, and the interactions between them; however, for the purposes of this research, the c-wave was not recorded or analyzed.

Under dim red light prior to and at each time point after CNV induction and DDS injection, ERG experiments were performed under scotopic conditions, with animals dark-adapted overnight prior to the experiment. Electroretinograms, in response to the full-field Ganzfeld stimulation, were recorded by a gold wire loop placed on the cornea. The reference and ground electrodes were 30 G platinum subdermal needle electrodes (SAFELEAD™ F-E2, Grass Products, Natus Neurology, Warwick, R.I., USA) inserted into the cheek and nape of the neck, respectively. A-wave and b-wave intensity responses were recorded by presenting single flashes of increasing intensity ($5 \times 10^{-4}$ to 305.7 sc cd·s·m$^{-2}$) and allowing the eye to dark adapt for 1 min after each flash. The intensity-response values for the a-wave and b-wave were fit with the Naka-Rushton equation, to determine a half-saturation intensity of the responses and maximal response.

Prior to treatment, post-treatment, and weekly thereafter, intraocular pressure (IOP) measurements were taken using an applanation tonometer (TONO-PEN®XL, Medtronic, Minneapolis, Minn., USA). The tono-pen has been shown to effectively measure rat IOP. It should be noted that general anesthesia, including combined ketamine and xylazine, has been shown to induce rapid and substantial decreases in IOP as well as increased inter-animal variability in IOPs.

A confocal scanning laser ophthalmoscope (cSLO) system (Heidelberg Retina Angiograph (HRA), Heidelberg Engineering, Heidelberg, Germany) was used to image the retina. FA still images were captured at 1-2 min, 10 min and 20 min after IP injection of 0.5 mL of 20% fluorescein dye (Sigma Aldrich, St. Louis, Mo., USA) and were used for quantification of CNV lesion areas. All data was acquired prior to treatment and at 1, 2, 4, 8, and 12 weeks post-injection.

CNV lesion areas were quantified using late-phase FA images. The use of late-phase (20 min) images allows time for the fluorescein to clear the normal vasculature, preventing vessel hyperfluorescence from interfering with area measurements. Additionally, only images that were centered on the lesion, well-focused on the choroid, non-saturated, and had even illumination were used to quantify CNV.

An example of image processing using ImageJ is presented in FIG. 7. The multi-Otsu thresholding (MOT) plugin for ImageJ was set to three levels, or "regions," defined as: background (FIG. 7B), diffuse leakage (non-hyperfluorescent leakage; FIG. 7C), and CNV (hyperfluorescent leakage; FIG. 7D). The threshold value within ImageJ is then adjusted to include all pixels within the "Region 2" (CNV) plug-in output. The CNV lesion was then outlined by the user, being careful to avoid vessels and other non-lesion pixels (FIG. 7E). The measured number of pixels was then converted into area using a scaling factor based on the optical properties of the rat eye and field of view of the image using the equation:

$$SF = \frac{\pi}{180} \times N'F' \times \frac{FOV}{RES}$$

where SF is the scaling factor in square micrometers per pixel, N'F' is the distance from the second nodal point of the eye to the retina in micrometers, FOV is the field of view in degrees, and RES is the length of the image in pixels. For the Long-Evans rats used in this study, SF was 3.35 μm$^2$. Note that within ImageJ, the MOT plugin requires an 8-bit grayscale image and measurements must be set to "Limit to threshold" under the "Analyze>Set measurements . . . " tab, otherwise all pixels within the outline will be counted rather than only within the lesion.

The parameter values obtained from the Naka-Rushton analyses and IOP measurements were compared using the paired t-test verses control. To determine significant differences in CNV lesion areas, one-way ANOVA was performed and all pairwise multiple comparisons were done using the Holm-Sidak method. Unless otherwise noted, significance represents $p<0.05$. All values are reported as sample mean±standard error of the mean.

In a previous, thorough evaluation of non-drug-loaded thermo-responsive hydrogel, no adverse effects were observed out to four weeks post-IVT injection. As the microsphere-hydrogel DDS was to be evaluated over the course of 12 weeks, an additional ocular health and safety evaluation was performed including ERG analysis and IOP measurements.

Figure 8:
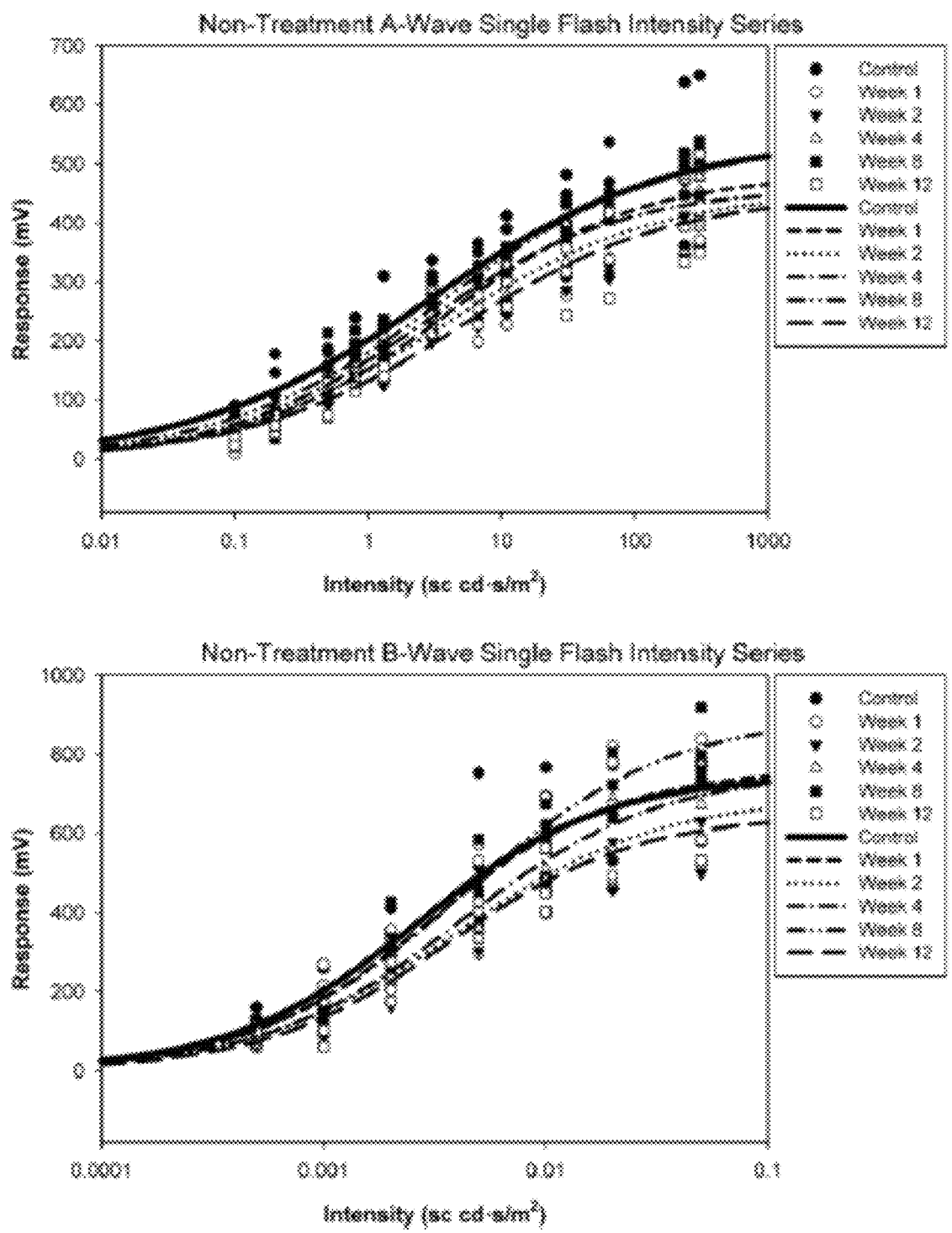
FIG. 8 shows average single flash ERG intensity-response functions for non-treated animals (top, a-wave; bottom, b-wave). Lines are the results of the Naka-Rushton analysis to the cumulative pool of data points and symbols represent different time points of investigated time frame. No significant differences were seen in either maximal a- and b-wave response or half-maximal a- and b-wave response.
Figure 9:
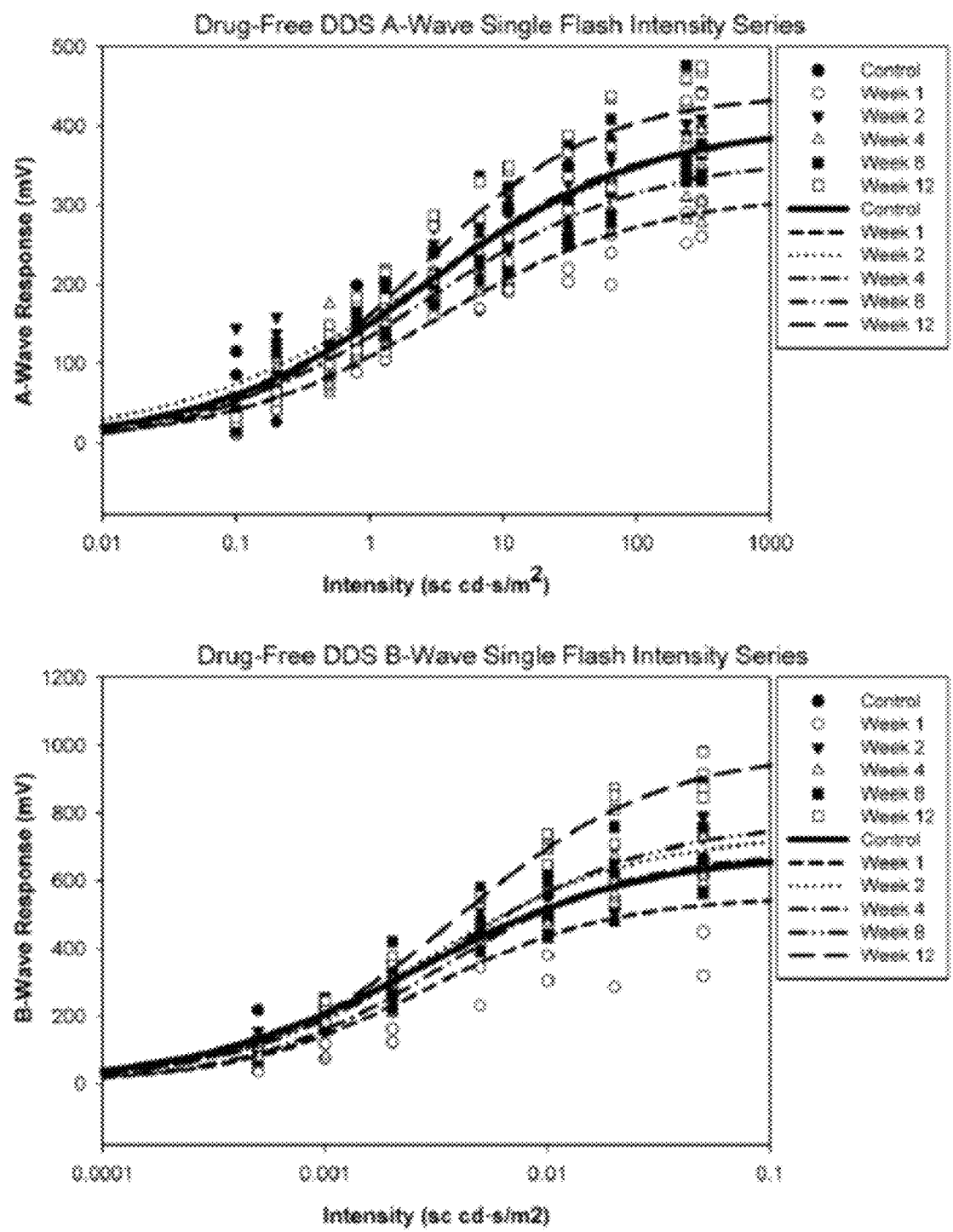
FIG. 9 shows average single flash ERG intensity-response functions for drug-free DDS treated animals (top, a-wave; bottom, b-wave). Lines are the results of the Naka-Rushton analysis to the cumulative pool of data points and symbols represent different time points of investigated time frame. A significant difference in maximal b-wave response is seen between Control and Week 12 ($p<0.05$). No significant difference in half-maximal a- or b-wave response was observed.
Figure 10:
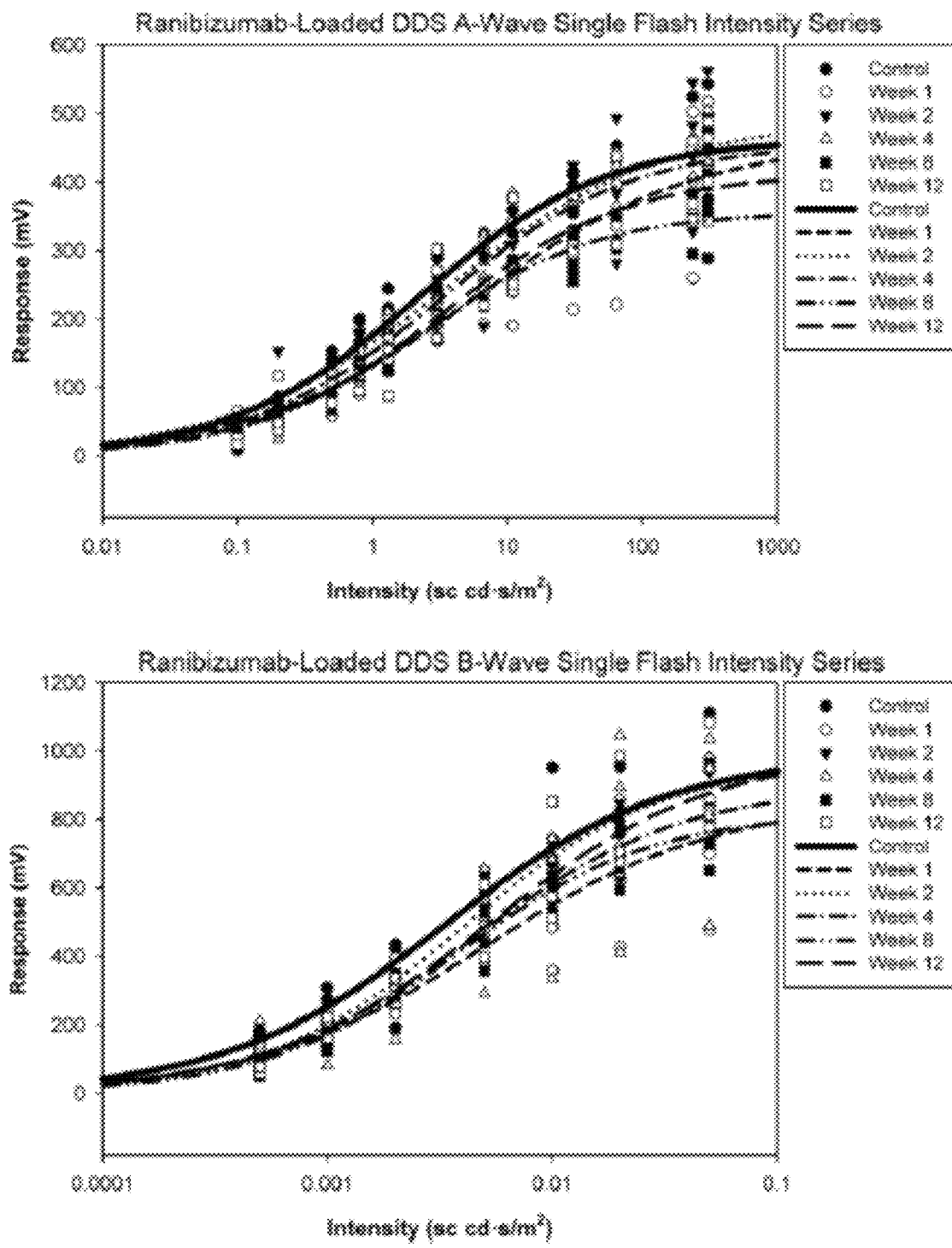
FIG. 10 shows average single flash ERG intensity-response functions for ranibizumab-loaded DDS treated animals (top, a-wave; bottom, b-wave). Lines are the results of the Naka-Rushton analysis to the cumulative pool of data points and symbols represent different time points of investigated time frame. No significant differences were seen in either maximal a- and b-wave response or half-maximal a- and b-wave response.
Figure 11:
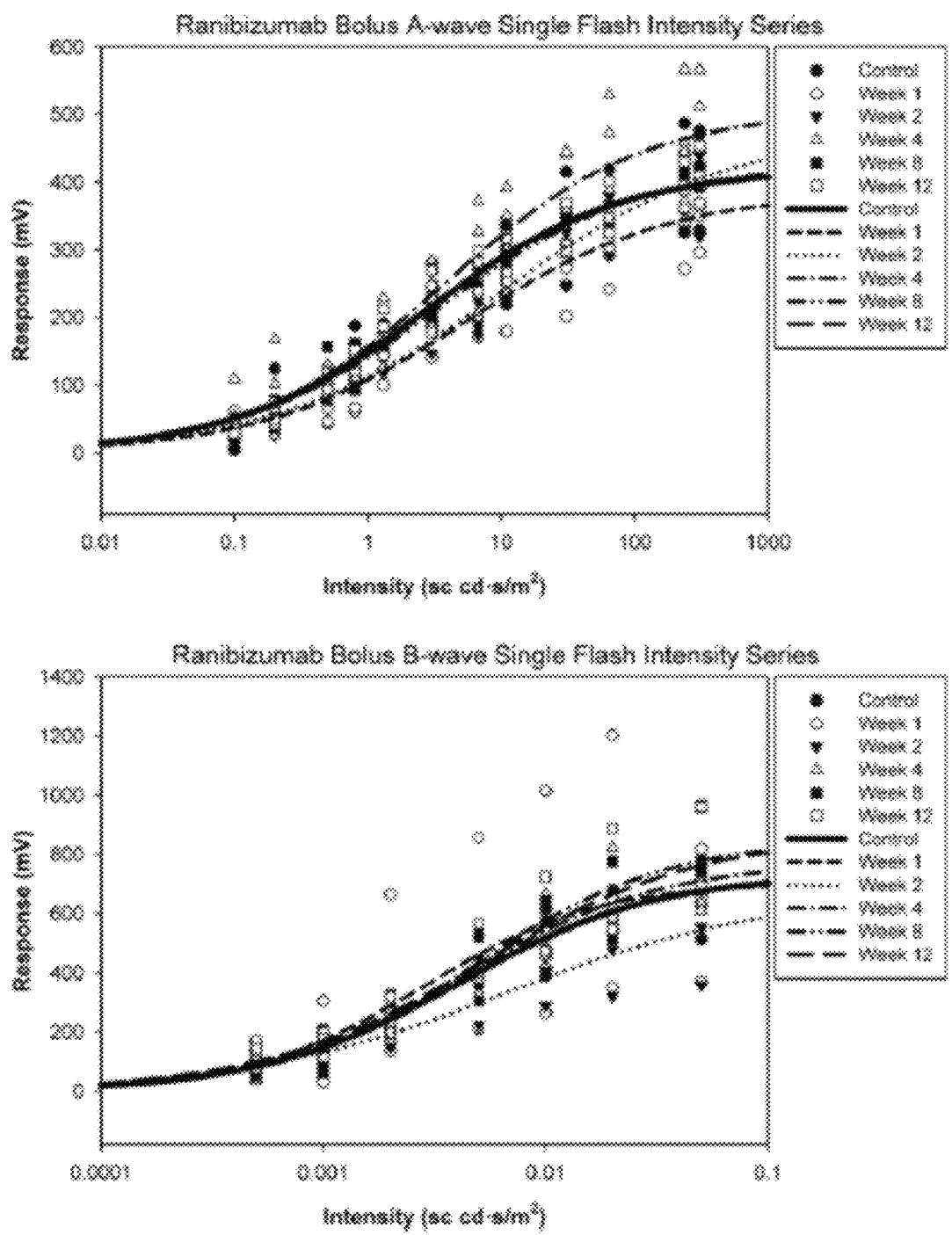
FIG. 11 shows average single flash ERG intensity-response functions for bolus ranibizumab treated animals (top, a-wave; bottom, b-wave). Lines are the results of the Naka-Rushton analysis to the cumulative pool of data points and symbols represent different time points of investigated time frame. No significant differences were seen in either maximal a- and b-wave response or half-maximal a- and b-wave response.
Figure 12:
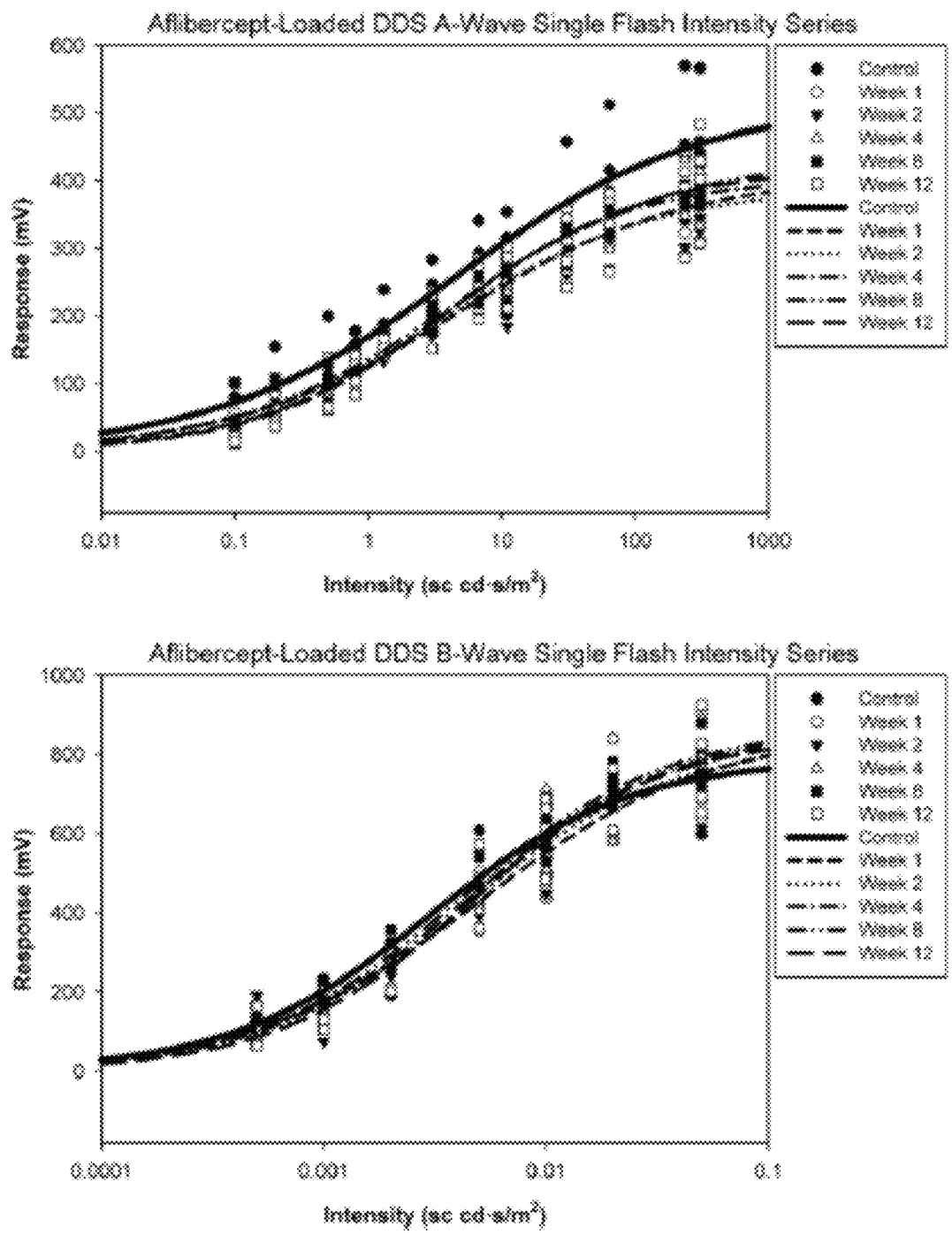
FIG. 12 shows average single flash ERG intensity-response functions for aflibercept-loaded DDS treated animals (top, a-wave; bottom, b-wave). Lines are the results of the Naka-Rushton analysis to the cumulative pool of data points and symbols represent different time points of investigated time frame. A significant difference in maximal a-wave response is seen between Control and Week 1-Week 12 ($p<0.05$). No significant difference in half-maximal a- or b-wave response was observed.
Figure 13:
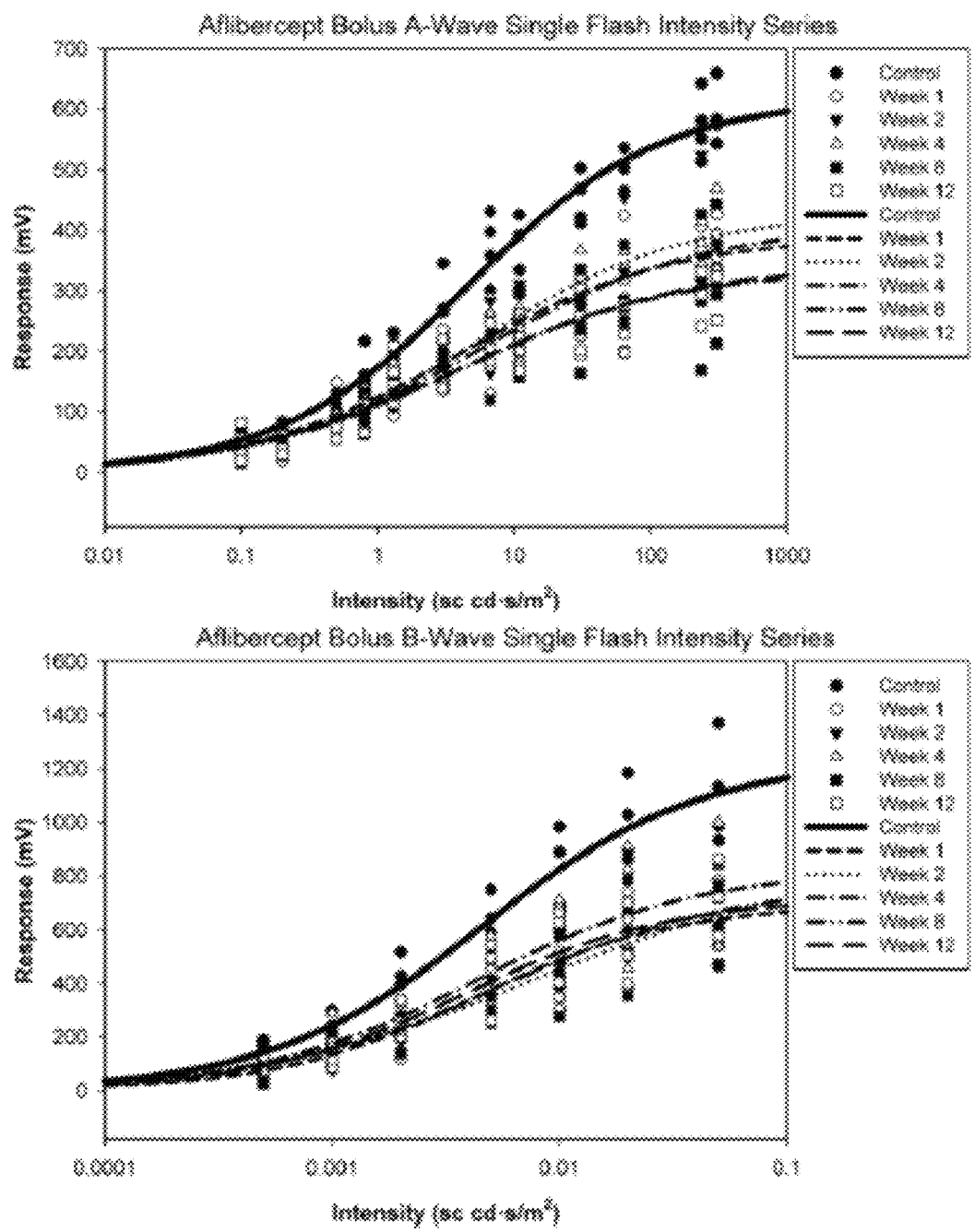
FIG. 13 shows average single flash ERG intensity-response functions for bolus aflibercept treated animals (top, a-wave; bottom, b-wave). Lines are the results of the Naka-Rushton analysis to the cumulative pool of data points and symbols represent different time points of investigated time frame. A significant difference in maximal a-wave response is seen between Control and Week 1-Week 12 ($p<0.05$). Additionally, a significant difference in maximal b-wave response is seen between Control and Week 1-Week 12 ($p<0.05$). No significant difference in half-maximal a- or b-wave response was observed.

The outer retina was evaluated by the a-wave, which reflects the activity of the photoreceptors. The sensitivity of the a-wave was examined through comparison of parameters obtained from the Naka-Rushton analyses and the intensity-response of the a-wave was determined before (control) and after injection of the DDS and the bolus drug counterparts. As was expected, no significant differences were seen in maximal a-wave response (control: 543.1±51.7 mV) or half-saturation intensity (control: 2.9±1.6 sc cd·s·m$^2$) of non-treated animals (FIG. 8, top). Additionally, no significant differences in a-wave parameters were seen for drug-free DDS treated animals (control Amax: 400.9±23.7 mV, control σA: 2.6±0.8 sc cd·s·m$^{-2}$; FIG. 9, top). For both the ranibizumab-loaded DDS (control Amax: 464.1±19.9 mV, control σA: 2.2±0.5 sc cd·s·m$^{-2}$) and bolus ranibizumab (control Amax: 419.9±24.0 mV, control σA: 2.6±0.8 sc cd·s·m$^{-2}$) treated animals, no significant differences were seen in a-wave parameters (FIGS. 10 and 11, top; respectively). However, for both the aflibercept-loaded DDS and bolus aflibercept treated animals, a significant difference in maximal a-wave response is seen between control and Week 1-Week 12 ($p<0.05$). For the aflibercept-loaded DDS treated animals, the maximal a-wave response post-treatment was ~20% lower than control (Amax: 516.0 51.1 mV) at all time-points post-treatment (FIG. 12, top) and for the bolus aflibercept treated animals, it was ~40% (control Amax: 616.4±25.4 mV; FIG. 13, top). No significant difference in half-saturation intensity was observed for either aflibercept-loaded DDS (control σA: 4.5±2.5 sc cd·s·m$^{-2}$) or bolus aflibercept (control σA: 4.6±0.9 sc cd·s·m$^{-2}$) treated animals.

Inner retinal function was evaluated by the b-wave, which reflects the activity of the bipolar cells and/or Müller cells. As with the a-wave, the sensitivity of the b-wave was examined through comparison of parameters obtained from the Naka-Rushton analyses and the intensity-response of the b-wave was determined before (control) and after injection of the DDS and the bolus drug counterparts. As expected, no significant differences were seen in maximal b-wave response (control: 748.5±70.7 mV) or half-saturation intensity (control σB: 2.6×10-3±8.0×10-4 sc cd·s·m$^{-2}$) of non-treated animals (FIG. 8, bottom). A significant increase of ~35% in maximal b-wave response was seen only at Week 12 compared to control for drug-free DDS treated animals (control B max: 684.7±37.8 mV; FIG. 9, bottom; $p<0.05$), suggesting that the DDS may cause a greater depolarization of the ON-bipolar cells of the retina in the long-term. Similar to the a-wave, for both the ranibizumab-loaded DDS (control Bmax: 987.9±91.0 mV, control σB: 3.3×10$^{-3}$±1.0×10$^{-3}$ sc cd·s·m$^{-2}$) and bolus ranibizumab treated animals (control Bmax: 734.3±65.0 mV, control σB: 4.1×10$^{-3}$±1.1×10$^{-3}$ sc cd·s·m$^{-2}$), no significant differences were seen in b-wave parameters after treatment (FIGS. 10 and 11, bottom; respectively). For the aflibercept-loaded DDS treated animals, no significant differences in b-wave parameters were observed (control Bmax: 790.4±51.8 mV, control σB: $3.0 \times 10^{-3} \pm 6.0 \times 10^{-4}$ sc cd·s·m$^{-2}$; FIG. 12, bottom). Surprisingly, for the bolus aflibercept treated animals, a significant decrease in maximal b-wave response is seen post-treatment through Week 12, with the maximal b-wave response being ~45% lower than controls (control Bmax: 1236.1±121.5 mV, control σB: $4.6 \times 10^{-3} \pm 1.4 \times 10^{-3}$ sc cd·s·m$^{-2}$; FIG. 13, bottom). Although a significant decrease in maximal b-wave response was seen in these animals after treatment, control maximal a- and b-wave responses for these animals were >50% higher than all other control measurements, which may suggest abnormal experimental conditions during control ERG measurements (e.g., residual eye drops enhancing the contact of the cornea electrode or the position of the eye being closer to the flash stimulus than normal).

IOP measurements were recorded prior to and immediately after IVT injection and at every time point thereafter. Table 2 shows the average IOP measurements for all treatment groups at each time point. The average control IOP values for all animals was 18.8±0.1 mmHg. As was anticipated, a significant increase of ~37% in IOP is seen immediately after IVT injection in all treated animals (p<0.05). Increased IOP remained at Week 1 for the aflibercept-loaded DDS and both bolus treated animals (23.3±1.0 and 25.0±1.8 mmHg, respectively). By Week 2, only bolus aflibercept treated animals had increased IOP (25.0±1.8 mmHg). Interestingly, at Weeks 8-12, the ranibizumab-loaded DDS treated animals had significantly lower IOP verses control (17.0±0.8 and 17.3±1.0 mmHg, respectively) and at Week 12, bolus ranibizumab treated animals also had significantly decreased IOP (17.3±1.5 mmHg). It should be noted that all IOP values were well within the range of what is normal in rats (15-25 mmHg).

animals exhibited smaller CNV lesion areas than bolus ranibizumab treated animals, however this difference was not significant. Furthermore, bolus ranibizumab treated animals only had a significant decrease in lesion area at Week 12. Bolus aflibercept treated animals had significantly smaller CNV lesions compared to non-treated animals and aflibercept-loaded DDS at Week 1, however it is unknown whether this difference is meaningful as CNV growth is not fully developed until ~10 days. Additionally, bolus aflibercept treated animals had significantly smaller CNV lesions compared to non-treated animals at Week 4 and Week 12. However, by Week 8, aflibercept-loaded DDS treated animals had significantly smaller CNV lesions than bolus and DDS treated animals from Week 8-Week 12 (p<0.05).

For both anti-VEGF-loaded DDSs, it is important to note that significant decreases in CNV lesion growth were achieved that exceeded that of bolus administration in the long term. With a 5 μL bolus injection of a clinical dose of either anti-VEGF, 50 μg of ranibizumab or 200 μg of aflibercept was delivered. In comparison, over the course of 12 weeks only ~450 ng of ranibizumab or ~200 ng aflibercept was delivered from the DDS of this invention. Thus, there is great potential of controlled and extended release from the DDS of this invention in the treatment of CNV.

The efficacy of the DDS to treat laser-induced CNV in rats was evaluated in addition to determining the safety and biocompatibility of the DDS. Retinal cellular function was evaluated using ERG parameters determined by fitting the intensity-response curve to the Naka-Rushton equation. Intraocular pressure measurements were also taken. Finally, CNV lesion areas were measured at every time point to determine whether the DDS effectively treated laser-induced CNV in Long-Evans rats.

In animals treated with the drug-free DDS, photoreceptor cellular function was maintained and normal ERG activity was observed throughout the 12 weeks post-treatment. This

TABLE 2

Average intraocular pressure measurements for all treatment groups

| Treatment | Control | Post-Injection | Week 1 | Week 2 | Week 4 | Week 8 | Week 12 |
|---|---|---|---|---|---|---|---|
| Non-treatment | 17.3 ± 2.1 | — | 22.0 ± 4.0 | 19.3 ± 0.6 | 19.0 ± 0.0 | 19.7 ± 0.6 | 17.3 ± 1.2 |
| Drug-free DDS | 19.0 ± 2.4 | 25.5 ± 4.4* | 21.8 ± 1.3 | 21.8 ± 1.5 | 21.3 ± 1.0 | 19.0 ± 0.8 | 18.8 ± 1.5 |
| Rani.-gel | 19.5 ± 1.3 | 27.0 ± 0.8* | 21.5 ± 1.7 | 20.8 ± 1.3 | 20.8 ± 1.0 | 17.0 ± 0.8* | 17.3 ± 1.0* |
| Rani.-bolus | 20.0 ± 2.2 | 26.5 ± 1.3* | 24.3 ± 1.7 | 20.3 ± 2.2 | 20.0 ± 2.0 | 19.8 ± 1.7 | 17.3 ± 1.5* |
| Aflib.-gel | 18.5 ± 1.3 | 25.0 ± 3.6* | 23.3 ± 1.0* | 20.8 ± 1.0 | 18.5 ± 2.1 | 19.8 ± 1.0 | 18.3 ± 1.3 |
| Aflib.-bolus | 18.0 ± 1.4 | 26.5 ± 1.7* | 25.0 ± 1.8* | 20.8 ± 1.0* | 18.5 ± 1.3 | 19.3 ± 2.2 | 17.8 ± 1.5 |

*Significant differences in IOP compared to each treatments' control measurement (p < 0.05)

Figure 14:
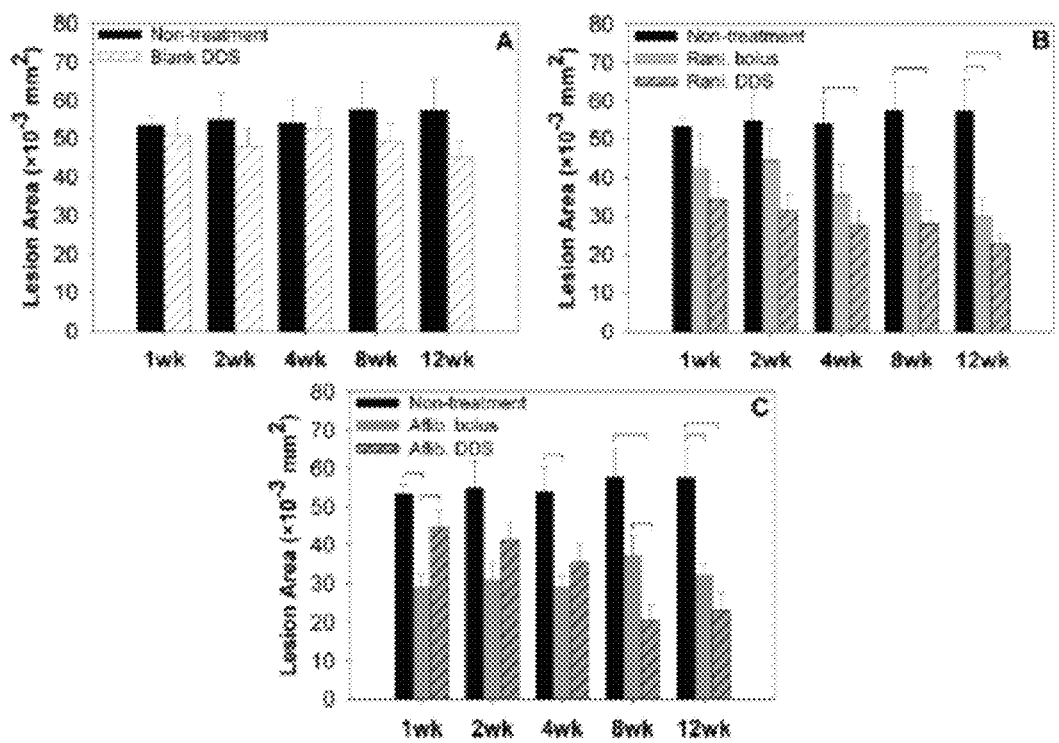
FIG. 14 shows CNV lesion areas for all treatment groups. Although CNV is assumed to not be fully developed at Week 1, it is presented for completeness: A) No significant difference is seen between non-treated animals and drug-free DDS treated animals ("Blank DDS") at any time point; B) ranibizumab-loaded DDS treated animals exhibited a significant decrease in CNV lesion areas from Week 4-Week 12 compared to non-treated animals whereas bolus ranibizumab treated animals only had a significant decrease in lesion area at Week 12; and C) bolus aflibercept treated animals had significantly smaller CNV lesions compared to non-treated animals at Week 4 and Week 12. However, aflibercept-loaded DDS treated animals had significantly smaller CNV lesions than bolus treated animals from Week 8-Week 12 ($p<0.05$).
Figure 15:
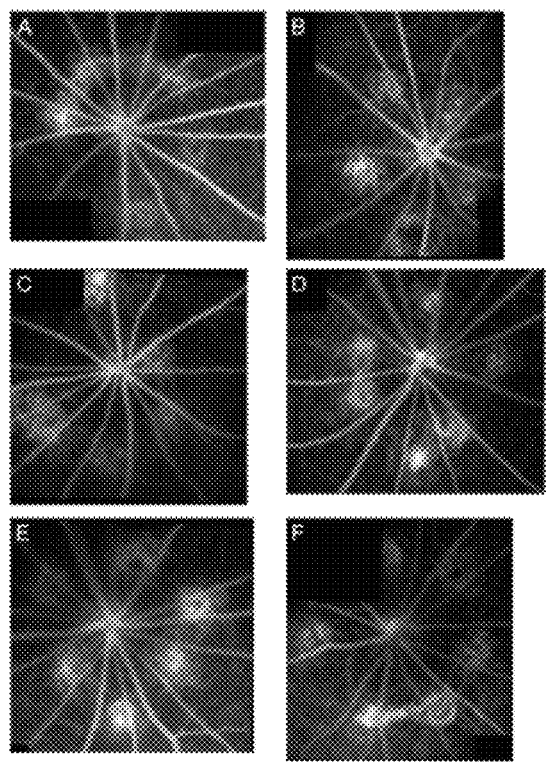
FIG. 15 shows representative composite FA images from Week 12 of treatment groups: A) non-treatment, B) drug-free DDS, C) ranibizumab bolus, D) ranibizumab-loaded DDS, E) aflibercept bolus, and F) aflibercept-loaded DDS. As is seen, 5-6 CNV lesions were induced in each treatment group and the severity of the lesions were approximately the same at Week 12.

The MOT technique effectively delineated the CNV lesion from the surrounding retina in the experimental laser model, allowing for objective quantification of CNV lesion areas. The CNV lesion areas for all treatment groups can be seen in FIG. 14. Representative composite FA images show that the severity of CNV lesions at Week 12 for each treatment group was approximately the same (FIG. 15). Although CNV is assumed to not be fully developed at Week 1, it has been presented for completeness. As anticipated, no significant difference was observed between non-treated animals and drug-free DDS treated animals at any time point. From Week 4-Week 12, the ranibizumab-loaded DDS had significantly smaller lesion areas than non-treated animals and by Week 12, these treated animals had CNV lesion areas that were 60% smaller (p<0.0002). Additionally, beginning on Week 1, ranibizumab-loaded DDS treated result expands the time frame for which the thermo-responsive hydrogel DDS has been shown to cause no long-term physiological effects on the outer retina. In a previous study, the thermo-responsive hydrogel was evaluated for four weeks and it did not cause any long-term physiological effects on the photoreceptors. The lack of change in the outer retina was not surprising as the photoreceptor cells are located farthest from the hydrogel injection. It follows, then, that the inner retinal cells are more likely to experience any adverse effects due to the hydrogel injection, and changes in inner retinal function would be apparent in the b-wave. As was shown, inner retinal health and activity was maintained through Week 8. Interestingly, a ~35% increase in maximal b-wave response was observed at Week 12 in all animals, which could imply a meaningful adverse effect in long-term biocompatibility. However, no significant changes in a- or b-wave half-saturation intensity, which indicates the sensitivity of the retina to illumination, were seen in any treatment group throughout the entire study. The human rod system requires an intensity change of greater than 14% for an observer to perceive a change in light intensity. Thus, while no change in half-maximal sensitivity was observed, it is possible that the large increase in maximal b-wave response observed caused perceptible changes in the rodent's vision whereby the rat was more sensitive to light at Week 12 compared to control.

For both the bolus ranibizumab and ranibizumab-loaded DDS treated animals, no significant differences were seen in either maximal a- and b-wave response or half-maximal a- and b-wave response, further indicating that the DDS does not induce adverse effects on retinal activity. Although no changes were observed in maximal b-wave parameters, a small by significant decrease (~10%) was observed in aflibercept-loaded DDS treated animals after treatment. For reasons mentioned above, this slight decrease would likely not cause perceptible changes in the rodent's vision. More surprising was the large (~40%), sustained decrease in maximal a- and b-wave responses for bolus aflibercept treated animals subsequent post-treatment. These bolus treated animals had a similar number and severity of lesions as the other treated groups (FIG. 14), which eliminates the possibility that the decrease in the full-field ERG maximal a- and b-wave responses was due to greater CNV area (i.e., decreased retinal activity). However, control measurements for these animals were >50% higher than all other control measurements, which may suggest abnormal experimental conditions during control ERG measurements (e.g., residual eye drops enhancing the contact of the cornea electrode or the position of the eye being closer to the flash stimulus than normal). In the future, histological evaluation of the enucleated eyes will confirm whether this sustained decrease in maximal a- and b-wave response was due to irreversible toxic retinal damage.

The clinical dose of aflibercept (50 μL injection of 40 mg/mL aflibercept) when injected into the human vitreous (3.8 mL) yields a vitreal concentration of 0.52 mg/mL. In this study, 5 μL of 40 mg/mL aflibercept was injected into the rat vitreous (13.6 μL vitreous volume), which translates into a vitreal concentration of 10.8 mg/mL, which is a much higher vitreal concentration than that used in humans. In a recent ex vivo study on the electrophysiological toxicity testing of aflibercept in bovine retina, a significant decrease (43.1%) in the maximal scotopic b-wave response was observed directly after exposure to 0.1 mg/mL aflibercept. After washing away the aflibercept, the b-wave response was no longer significantly decreased. So, it is possible that for rats, the high bolus aflibercept concentration used in this study caused irreversible toxic retinal damage. However, in a study in chinchilla rabbits, a clinical dose of aflibercept was administered and with a vitreous volume of approximately 200-300 μL, this translates into a vitreal concentration of 6.67-10 mg/mL. It was found that this high vitreal concentration did not alter any ERG parameters at 24 hr or 7 days after treatment; however, rabbits were only dark-adapted for 30 minutes prior to ERG recordings and this is an insufficient amount of time for complete dark-adaptation to occur. Importantly, the decreased maximal a- and b-wave responses in bolus aflibercept treated animals was mediated by using the DDS as aflibercept is delivered slowly over time and at much lower concentrations (i.e., two orders of magnitude less) and no changes in ERG parameters were observed in aflibercept-loaded DDS treated animals.

Retinal function can also be affected by changes in IOP. In the current study, there was a significant increase in comparison to control in TOP measurements immediately after the injection, which resolved by Week 2 for all treatment groups. This indicates that the IVT injection of the DDS of this invention had minimal impact on IOP. Surprisingly, in the bolus ranibizumab and ranibizumab-loaded DDS treated animals, a significant decrease in IOP was observed at later time points. However, all values obtained in this study are in agreement with the normal range of IOPs for Long-Evans rodents. Although the adult rat vitreous volume is ~14 μL, IVT injection volumes of up to 5 μL have been shown by Dureau et al. (2001) to have good reproducibility with minimal loss of injected solution. Therefore, any changes seen in the ERG parameters were likely not the result of altered IOP. Based on the ERG parameter analysis of the drug-free DDS and the IOP values for all treatment groups, it is believed that the DDS is safe, biocompatible, and well-tolerated.

No significant differences were seen between non-treated and drug-free DDS animals at any time point. This suggests that the significant decreases in CNV lesion areas observed in bolus or anti-VEGF-loaded DDS treated animals were in fact related to the anti-VEGF treatment. It has been demonstrated that much less drug delivered constantly yields a better treatment outcome than a bolus injection in the long term. Ranibizumab-loaded DDS treated animals exhibited a significant decrease in CNV lesion areas from Week 4-Week 12 compared to non-treated animals whereas bolus ranibizumab treated animals only had a significant decrease in lesion area at Week 12. Due to the short half-life of ranibizumab (t1/2=9 days), after 12 weeks, the ranibizumab that was delivered via bolus injection was effectively gone. It is important to note that ranibizumab was administered immediately after CNV induction and that a sufficiently high vitreal concentration of ranibizumab dose present during the highest rate of blood vessel growth (3-10 days after induction), which correlates with the peak expression of VEGF and its receptor. This may imply that the large initial bolus ranibizumab dose prevented CNV from fully forming and thus allowed CNV lesion areas to significantly decrease by Week 12.

Bolus aflibercept treated animals had significantly smaller CNV lesions compared to non-treated animals at Week 4 and Week 12. However, aflibercept-loaded DDS treated animals had significantly smaller CNV lesions than bolus treated animals from Week 8-Week 12. Thus, the aflibercept-loaded DDS had greater efficacy in the long-term. Aflibercept is a more potent anti-VEGF than ranibizumab as demonstrated clinically by the need to administer ranibizumab more often than aflibercept to achieve a similar treatment outcome. This may explain the early advantage of bolus aflibercept compared to the DDS, yet extended delivery of aflibercept significantly reduced CNV lesion areas even though the rate of release for aflibercept from the DDS was 2.3× less than that of ranibizumab.

Interestingly, both anti-VEGF-loaded DDSs had roughly the same decreased CNV lesion areas at Week 12, with aflibercept-loaded DDS areas only 2% larger than the ranibizumab-loaded DDS areas. In our preliminary study on extended release of dexamethasone, a potent corticosteroid, from the DDS of this invention (nanospheres rather than microspheres), it has been demonstrated that extended release of dexamethasone from the DDS of this invention greatly reduced CNV lesions areas compared to bolus administration while delivering less than 5% of the amount of bolus dexamethasone. Together with the results presented here, this suggests that the efficacy of a variety of antiangiogenic agents could be greatly improved by controlled and extended release from the DDS of this invention.

There is debate as to whether bevacizumab, a humanized variant of the anti-human VEGF-A monoclonal antibody A.4.6.1, and ranibizumab, a humanized monoclonal antibody and derivative of bevacizumab, are effective in treating murine neovascularization. In a study evaluating the efficacy and safety of intravitreal injections of bevacizumab and ranibizumab in the treatment of CNV in a rat model, no therapeutic effect was observed out to 28 days over a range of doses both above and below the clinical dose of each drug. However, in several studies on the effect of using bevacizumab to treatment corneal neovascularization, humanized anti-VEGF was found to be effective in the rat. It has been shown that systemic or topical application of bevacizumab significantly inhibited inflammation-induced angiogenesis in the cornea of mice and that bevacizumab binds to mouse VEGF-A, which was determined by Western blot, enzyme-linked immunosorbent assay (ELISA), and plasmon resonance assay. Additionally, it has been demonstrated that topical bevacizumab limited corneal neovascularization in rats it has been found that sub-conjunctival injection of bevacizumab can significantly inhibit corneal angiogenesis. Furthermore, the results presented above clearly demonstrate the efficacy of ranibizumab in treating murine CNV.

In summary, controlled and extended release of anti-VEGFs from the DDS was shown to be more efficacious than bolus anti-VEGF treated animals in a laser-induced CNV murine model. Both anti-VEGF-loaded DDSs exhibited very similar efficacy at Week 12, suggesting that improved efficacy may extend to other antiangiogenic agents. Additionally, the DDS was shown to be safe, biocompatible, and well-tolerated, with no long-term adverse effects observed in drug-free DDS treated animals.

Thus, the invention provides a new and improved method to deliver anti-VEGF or other treatment agent for an extended period of time. Currently, there are over 4 million intravitreal injections done monthly in U.S. alone to treat AMD, DR and other vascular disease. Limiting injection to every 6 months will have a great socioeconomic impact as well as reduce potential side effects of monthly intravitreal injections.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A method of delivering a compound to an eye, the method comprising:
applying to or into an eye of a mammal a composition in a first physicochemical state, wherein the composition comprises a treatment agent microencapsulated in degradable thermo-responsive hydrogel, wherein the degradable microcapsules comprise polyethylene glycol (PEG), $Mg(OH)_2$, bovine serum albumin, and sucrose;
wherein the composition changes to a second physicochemical state upon administration, wherein the second physicochemical state is more solid than the first physicochemical state, and wherein the degradable microcapsules release the microencapsulated treatment agent over time after applying.

2. The method of claim 1, wherein the composition further comprises a non-encapsulated treatment agent dispersed within the degradable thermo-responsive hydrogel.

3. The method of claim 1, wherein the microencapsulated treatment agent comprises an anti-VEGF agent, an anti-PDGF agent, cells, delivery cells, antibiotic, a corticosteroid, enzymes, peptides, nucleic acids, or combinations thereof.

4. The method of claim 3, wherein the degradable microcapsules comprise copolymers of poly(lactic-co-glycolic acid) and chitin, polyethylene glycol, or diacrylate.

5. The method of claim 4, wherein the microencapsulated treatment agent comprises poly(lactic-co-glycolic acid), poly(lactic acid), polysaccharide chitin, alginate, or combinations or block copolymers thereof.

6. The method of claim 1, wherein the hydrogel comprises poly(N-isopropylacrylamide), poly(latic acid), polysaccharide chitin, alginate, diacrylate, or combinations or block copolymers thereof.

7. The method of claim 1, wherein the second physicochemical state is degradable to release the microencapsulated treatment agent and further comprising controlling the degradation by type and/or amount of crosslinking to control the release of the microencapsulated treatment agent.

8. The method of claim 1, wherein the composition comprises a second microencapsulated treatment agent suspended in the thermo-responsive hydrogel, the second microencapsulated treatment agent having a different rate of release than the microencapsulated treatment agent.

9. The method of claim 1, further comprising applying the composition in a first physicochemical state by intravitreal injection, by periocular or transcleral injection, by topical application, by intracameral application, by suprachoroidal application, within ocular implants, or combinations thereof.

10. The method of claim 1, further comprising applying the composition in a first physicochemical state by small gauge needle or microcatheter.

11. The method of claim 1, further comprising applying the composition in a first physicochemical state as a scleral structure during retinal detachment treatment.

12. The method of claim 1, wherein the hydrogel is thermo-responsive at a physiological temperature of about 32° C. to about 37° C.

13. The method of claim 1, wherein the thermo-responsive hydrogels are in a liquid-like state at room temperature and more solid state at body temperature.

14. The method of claim 1, wherein the degradable microcapsules release the microencapsulated treatment agent over 196 days after applying.

15. A method of delivering a compound to an eye, the method comprising:
applying to or into an eye of a mammal a composition in a first physicochemical state, wherein the composition comprises a treatment agent microencapsulated in degradable microcapsules that are suspended in a degradable thermo-responsive hydrogel, wherein the thermo-responsive hydrogels comprise a liquid-like state at room temperature and a more solid state at body temperature, and the suspended degradable microcapsules comprise poly(lactic-co-glycolic acid), polyethylene glycol (PEG), $Mg(OH)_2$, bovine serum albumin, and sucrose;
wherein the composition changes to a second physicochemical state upon administration, wherein the second physicochemical state is more solid than the first physicochemical state, and wherein the degradable microcapsules release the microencapsulated treatment agent over six months after applying.

16. The method of claim 15, wherein the degradable microcapsules comprise copolymers of the poly(lactic-co-glycolic acid) and chitin, polyethylene glycol, or diacrylate.

17. The method of claim 15, wherein the second physicochemical state is degradable to release the microencapsulated treatment agent and further comprising controlling the hydrogel degradation by type and/or amount of crosslinking to control the release of the microencapsulated treatment agent.

18. The method of claim 17, wherein the composition comprises a second microencapsulated treatment agent suspended in the thermo-responsive hydrogel, the second microencapsulated treatment agent having a different rate of release than the microencapsulated treatment agent.

19. The method of claim 17, wherein the composition further comprises a non-encapsulated treatment agent dispersed within the degradable thermo-responsive hydrogel.

20. A method of delivering a compound to an eye, the method comprising:
applying to or into an eye of a mammal a composition in a first physicochemical state, wherein the composition includes a microencapsulated treatment agent suspended in a degradable thermo-responsive hydrogel, wherein the microencapsulated treatment agent comprises degradable microcapsules formed of poly(lactic-co-glycolic acid), polyethylene glycol (PEG), $Mg(OH)_2$, bovine serum albumin, and sucrose;
wherein the composition changes to a second physicochemical state upon administration, wherein the second physicochemical state is more solid than the first physicochemical state, and wherein the degradable microcapsules release the microencapsulated treatment agent over time after applying.

* * * * *